(12) United States Patent
Weisbart

(10) Patent No.: US 8,680,066 B2
(45) Date of Patent: Mar. 25, 2014

(54) METHODS FOR DETERMINING AND INHIBITING RHEUMATOID ARTHRITIS ASSOCIATED WITH THE BRAF ONCOGENE IN A SUBJECT

(75) Inventor: Richard H. Weisbart, Sepulveda, CA (US)

(73) Assignee: The United States of America as represented by the Development of Veterans Affairs, Washington, DC (US)

( * ) Notice: Subject to any disclaimer, the term of this patent is extended or adjusted under 35 U.S.C. 154(b) by 0 days.

(21) Appl. No.: 13/440,942

(22) Filed: Apr. 5, 2012

(65) Prior Publication Data

US 2012/0258461 A1    Oct. 11, 2012

Related U.S. Application Data

(60) Provisional application No. 61/472,119, filed on Apr. 5, 2011.

(51) Int. Cl.
*C12N 15/11*   (2006.01)
*C12Q 1/68*    (2006.01)

(52) U.S. Cl.
USPC .......................................... 514/44 A; 435/6.1

(58) Field of Classification Search
None
See application file for complete search history.

(56) References Cited

U.S. PATENT DOCUMENTS

2005/0019918 A1 * 1/2005 Sumimoto et al. ............ 435/375
2005/0277118 A1 * 12/2005 Roth et al. ........................ 435/6
2009/0099190 A1 * 4/2009 Flynn et al. .................... 514/249

FOREIGN PATENT DOCUMENTS

EP    2036990 A1 * 3/2009

\* cited by examiner

*Primary Examiner* — Tracy Vivlemore
*Assistant Examiner* — Kate Poliakova-Georgan
(74) *Attorney, Agent, or Firm* — Adriano & Associates

(57) ABSTRACT

The invention provides methods for determining whether a subject is suffering from a rheumatoid arthritis associated with the BRAF oncogene comprising contacting isolated fibroblasts from the subject with a molecule or pool of molecules directed to the BRAF oncogene; and culturing the sample in the presence of the agent and determining whether BRAF oncogene expression by the cell is decreased and/or whether cells in the sample return to a less transformed phenotype, exhibit decreased cell proliferation and/or exhibit increased contact inhibition, any of which is indicative that the subject is suffering from a rheumatoid arthritis associated with the BRAF oncogene.

17 Claims, 11 Drawing Sheets

B   RA6
siRNA
Control   BRAF
BRAF 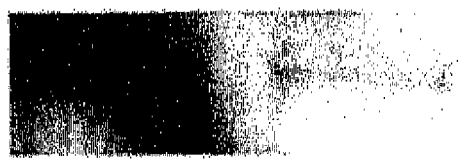
Actin 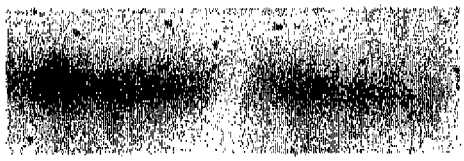
Figure 4 (continued)

CHARACTERIZATION OF BRAF, KRAS, & NRAS IN RHEUMATOID SYNOVIAL FIBROBLASTS

| RA Patient # | BRAF Aberrant Splice Variant | BRAF Mutation | BRAF Nucleotide Changes | KRAS Mutation | KRAS Nucleotide Changes | NRAS Mutation | NRAS Nucleotide Changes |
|---|---|---|---|---|---|---|---|
| 1 | None | V600R | GTG->AGG | D173N CL4<br>A83P CL6 | GAT->AAT<br>GCC->CCC | N94H CL5<br>T20A CL6<br>T50A CL6 | AAC->CAC<br>ACA->GCA<br>ACC->GCC |
| 2 | None | None | | None | | K49* CL3 | AAA->TAA |
| 3 | Δ exons 4-16 | None | | T74A CL3&4 | ACT->GCT | None | |
| 4 | None | None | | L23P CL4<br>K117E CL4 | CTA->CCA<br>AAA->GAA | N/A | |
| 5 | Δ exons 2-16 | None | | E31K CL1<br>K16AR CL1<br>E31Q CL2 | GAA->AAA<br>AAA->AGA<br>GAA->CAA | S87G CL1<br>K135R CL1<br>G180D CL2<br>R123G CL3 | AGC->GGC<br>AAG->AGG<br>GGT->GAT<br>AGG->GGG? |
| 6 | Δ exons 2-15 | V600R | GTG->AGG | E31G CL6<br>V103F CL6 | GAA->GGA<br>GTT->TTT | G48S CL1<br>K147R CL5<br>E3G CL7 | GGT->AGT<br>AAG->AGG<br>GAG->GGG |
| 7 | Δ exons 3-8 | None | | Q22R CL11<br>D47G CL12 | CAG->CGG<br>GAT->GGT | N/A | |
| 8 | Δ exons 4-13 | None | | None | | N/A | |
| 9 | Δ exons 4-16 | None | | K169M CL4<br>K172R CL4<br>L23P CL6<br>K117E CL8 | AAG->ATG<br>AAA->AGA<br>CTA->CCA<br>AAA->GAA | | |

Figure 6

SEQUENCE LISTING

```
<160> NUMBER OF SEQ ID NOS: 8

<210> SEQ ID NO 1
<211> LENGTH: 2301
<212> TYPE: DNA
<213> ORGANISM: Homo sapiens
<220> FEATURE:
```

```
<221> NAME/KEY: CDS
<222> LOCATION: (1)..(2301)
<220> FEATURE:
<221> NAME/KEY: misc_feature
<222> LOCATION: (1)..(138)
<223> OTHER INFORMATION: part of exon 1
<220> FEATURE:
<221> NAME/KEY: misc_feature
<222> LOCATION: (139)..(240)
<223> OTHER INFORMATION: exon 2
<220> FEATURE:
<221> NAME/KEY: misc_feature
<222> LOCATION: (139)..(735)
<223> OTHER INFORMATION: autoinhibitory domain from amino acid val47 to
      leu245
<220> FEATURE:
<221> NAME/KEY: misc_feature
<222> LOCATION: (241)..(504)
<223> OTHER INFORMATION: exon 3
<220> FEATURE:
<221> NAME/KEY: misc_feature
<222> LOCATION: (301)..(1038)
<223> OTHER INFORMATION: sequences encoding autoinhibitory domain of
      BRAF protein
<220> FEATURE:
<221> NAME/KEY: misc_feature
<222> LOCATION: (505)..(608)
<223> OTHER INFORMATION: exon 4
<220> FEATURE:
<221> NAME/KEY: misc_feature
<222> LOCATION: (609)..(711)
<223> OTHER INFORMATION: exon 5
<220> FEATURE:
<221> NAME/KEY: misc_feature
<222> LOCATION: (712)..(860)
<223> OTHER INFORMATION: exon 6
<220> FEATURE:
<221> NAME/KEY: misc_feature
<222> LOCATION: (861)..(980)
<223> OTHER INFORMATION: exon 7
<220> FEATURE:
<221> NAME/KEY: misc_feature
<222> LOCATION: (981)..(1140)
<223> OTHER INFORMATION: exon 8
<220> FEATURE:
<221> NAME/KEY: misc_feature
<222> LOCATION: (1141)..(1177)
<223> OTHER INFORMATION: exon 9
<220> FEATURE:
<221> NAME/KEY: misc_feature
<222> LOCATION: (1178)..(1314)
<223> OTHER INFORMATION: exon 10
<220> FEATURE:
<221> NAME/KEY: misc_feature
<222> LOCATION: (1297)..(2178)
<223> OTHER INFORMATION: sequences encoding kinase domain of BRAF
      protein
<220> FEATURE:
<221> NAME/KEY: misc_feature
<222> LOCATION: (1315)..(1432)
<223> OTHER INFORMATION: exon 11
<220> FEATURE:
<221> NAME/KEY: misc_feature
<222> LOCATION: (1433)..(1517)
<223> OTHER INFORMATION: exon 12
<220> FEATURE:
<221> NAME/KEY: misc_feature
<222> LOCATION: (1518)..(1694)
<223> OTHER INFORMATION: exon 13
<220> FEATURE:
<221> NAME/KEY: misc_feature
<222> LOCATION: (1695)..(1741)
<223> OTHER INFORMATION: exon 14
<220> FEATURE:
<221> NAME/KEY: misc_feature
<222> LOCATION: (1742)..(1860)
<223> OTHER INFORMATION: exon 15
<220> FEATURE:
<221> NAME/KEY: misc_feature
<222> LOCATION: (1798)..(1800)
```

<223> OTHER INFORMATION: BRAF codon 600 encoding valine; mutation at
      this position leading to activated BRAF protein associated with
      rheumatoid arthritis, such as a double mutation from GTG to AGG
      or CGG resulting in valine to arginine change at codon 600.
<220> FEATURE:
<221> NAME/KEY: misc_feature
<222> LOCATION: (1861)..(1992)
<223> OTHER INFORMATION: exon 16
<220> FEATURE:
<221> NAME/KEY: misc_feature
<222> LOCATION: (1993)..(2127)
<223> OTHER INFORMATION: exon 17
<220> FEATURE:
<221> NAME/KEY: misc_feature
<222> LOCATION: (2128)..(2301)
<223> OTHER INFORMATION: part of exon 18
<300> PUBLICATION INFORMATION:
<301> AUTHORS: Weisbart RH, Chan G, Heinze E, Mory R, Nishimura RN,
      Colburn K.
<302> TITLE: BRAF drives synovial fibroblast transformation in
      rheumatoid arthritis
<303> JOURNAL: J Biol Chem.
<304> VOLUME: 285
<305> ISSUE: 45
<306> PAGES: 34299-303
<307> DATE: 2010-11-05
<313> RELEVANT RESIDUES IN SEQ ID NO: (1798)..(1800)
<300> PUBLICATION INFORMATION:
<301> AUTHORS: Wan PT, Garnett MJ, Roe SM, Lee S, Niculescu-Duvaz D,
      Good VM, Jones CM, Marshall CJ, Springer CJ, Barford D, Marais R;
      Cancer Genome Project
<302> TITLE: Mechanism of activation of the RAF-ERK signaling pathway by
      oncogenic mutations of B-RAF
<303> JOURNAL: Cell
<304> VOLUME: 116
<305> ISSUE: 6
<306> PAGES: 855-67
<307> DATE: 2004-03-19
<313> RELEVANT RESIDUES IN SEQ ID NO: (1297)..(2178)
<300> PUBLICATION INFORMATION:
<301> AUTHORS: Tran NH, Wu X, Frost JA
<302> TITLE: B-Raf and Raf-1 are regulated by distinct autoregulatory
      mechanisms
<303> JOURNAL: J Biol Chem
<304> VOLUME: 280
<305> ISSUE: 16
<306> PAGES: 16244-53
<307> DATE: 2005-04-22
<313> RELEVANT RESIDUES IN SEQ ID NO: (301)..(1038)
<300> PUBLICATION INFORMATION:
<308> DATABASE ACCESSION NUMBER: NCBI Accession NM_004333.4
<309> DATABASE ENTRY DATE: 2009-11-01
<313> RELEVANT RESIDUES IN SEQ ID NO: (1)..(2301)

<400> SEQUENCE: 1

```
atg gcg gcg ctg agc ggt ggc ggt ggt ggc ggc gcg gag ccg ggc cag      48
Met Ala Ala Leu Ser Gly Gly Gly Gly Gly Gly Ala Glu Pro Gly Gln
1               5                   10                  15 gct ctg ttc aac ggg gac atg gag ccc gag gcc ggc gcc ggc gcc ggc      96
Ala Leu Phe Asn Gly Asp Met Glu Pro Glu Ala Gly Ala Gly Ala Gly
            20                  25                  30 gcc gcg gcc tct tcg gct gcg gac cct gcc att ccg gag gag gtg tgg     144
Ala Ala Ala Ser Ser Ala Ala Asp Pro Ala Ile Pro Glu Glu Val Trp
        35                  40                  45 aat atc aaa caa atg att aag ttg aca cag gaa cat ata gag gcc cta     192
Asn Ile Lys Gln Met Ile Lys Leu Thr Gln Glu His Ile Glu Ala Leu
    50                  55                  60 ttg gac aaa ttt ggt ggg gag cat aat cca cca tca ata tat ctg gag     240
Leu Asp Lys Phe Gly Gly Glu His Asn Pro Pro Ser Ile Tyr Leu Glu
65                  70                  75                  80 gcc tat gaa gaa tac acc agc aag cta gat gca ctc caa caa aga gaa     288
Ala Tyr Glu Glu Tyr Thr Ser Lys Leu Asp Ala Leu Gln Gln Arg Glu
                85                  90                  95
```

```
caa cag tta ttg gaa tct ctg ggg aac gga act gat ttt tct gtt tct    336
Gln Gln Leu Leu Glu Ser Leu Gly Asn Gly Thr Asp Phe Ser Val Ser
            100                 105                 110 agc tct gca tca atg gat acc gtt aca tct tct tcc tct tct agc ctt    384
Ser Ser Ala Ser Met Asp Thr Val Thr Ser Ser Ser Ser Ser Ser Leu
        115                 120                 125 tca gtg cta cct tca tct ctt tca gtt ttt caa aat ccc aca gat gtg    432
Ser Val Leu Pro Ser Ser Leu Ser Val Phe Gln Asn Pro Thr Asp Val
    130                 135                 140 gca cgg agc aac ccc aag tca cca caa aaa cct atc gtt aga gtc ttc    480
Ala Arg Ser Asn Pro Lys Ser Pro Gln Lys Pro Ile Val Arg Val Phe
145                 150                 155                 160 ctg ccc aac aaa cag agg aca gtg gta cct gca agg tgt gga gtt aca    528
Leu Pro Asn Lys Gln Arg Thr Val Val Pro Ala Arg Cys Gly Val Thr
                165                 170                 175 gtc cga gac agt cta aag aaa gca ctg atg atg aga ggt cta atc cca    576
Val Arg Asp Ser Leu Lys Lys Ala Leu Met Met Arg Gly Leu Ile Pro
            180                 185                 190 gag tgc tgt gct gtt tac aga att cag gat gga gag aag aaa cca att    624
Glu Cys Cys Ala Val Tyr Arg Ile Gln Asp Gly Glu Lys Lys Pro Ile
        195                 200                 205 ggt tgg gac act gat att tcc tgg ctt act gga gaa gaa ttg cat gtg    672
Gly Trp Asp Thr Asp Ile Ser Trp Leu Thr Gly Glu Glu Leu His Val
    210                 215                 220 gaa gtg ttg gag aat gtt cca ctt aca aca cac aac ttt gta cga aaa    720
Glu Val Leu Glu Asn Val Pro Leu Thr Thr His Asn Phe Val Arg Lys
225                 230                 235                 240 acg ttt ttc acc tta gca ttt tgt gac ttt tgt cga aag ctg ctt ttc    768
Thr Phe Phe Thr Leu Ala Phe Cys Asp Phe Cys Arg Lys Leu Leu Phe
                245                 250                 255 cag ggt ttc cgc tgt caa aca tgt ggt tat aaa ttt cac cag cgt tgt    816
Gln Gly Phe Arg Cys Gln Thr Cys Gly Tyr Lys Phe His Gln Arg Cys
            260                 265                 270 agt aca gaa gtt cca ctg atg tgt gtt aat tat gac caa ctt gat ttg    864
Ser Thr Glu Val Pro Leu Met Cys Val Asn Tyr Asp Gln Leu Asp Leu
        275                 280                 285 ctg ttt gtc tcc aag ttc ttt gaa cac cac cca ata cca cag gaa gag    912
Leu Phe Val Ser Lys Phe Phe Glu His His Pro Ile Pro Gln Glu Glu
    290                 295                 300 gcg tcc tta gca gag act gcc cta aca tct gga tca tcc cct tcc gca    960
Ala Ser Leu Ala Glu Thr Ala Leu Thr Ser Gly Ser Ser Pro Ser Ala
305                 310                 315                 320 ccc gcc tcg gac tct att ggg ccc caa att ctc acc agt ccg tct cct    1008
Pro Ala Ser Asp Ser Ile Gly Pro Gln Ile Leu Thr Ser Pro Ser Pro
                325                 330                 335 tca aaa tcc att cca att cca cag ccc ttc cga cca gca gat gaa gat    1056
Ser Lys Ser Ile Pro Ile Pro Gln Pro Phe Arg Pro Ala Asp Glu Asp
            340                 345                 350 cat cga aat caa ttt ggg caa cga gac cga tcc tca tca gct ccc aat    1104
His Arg Asn Gln Phe Gly Gln Arg Asp Arg Ser Ser Ser Ala Pro Asn
        355                 360                 365 gtg cat ata aac aca ata gaa cct gtc aat att gat gac ttg att aga    1152
Val His Ile Asn Thr Ile Glu Pro Val Asn Ile Asp Asp Leu Ile Arg
    370                 375                 380 gac caa gga ttt cgt ggt gat gga gga tca acc aca ggt ttg tct gct    1200
Asp Gln Gly Phe Arg Gly Asp Gly Gly Ser Thr Thr Gly Leu Ser Ala
385                 390                 395                 400
```

| | | |
|---|---|---|
| acc ccc cct gcc tca tta cct ggc tca cta act aac gtg aaa gcc tta<br>Thr Pro Pro Ala Ser Leu Pro Gly Ser Leu Thr Asn Val Lys Ala Leu<br>405 410 415 | 1248 |
| cag aaa tct cca gga cct cag cga gaa agg aag tca tct tca tcc tca<br>Gln Lys Ser Pro Gly Pro Gln Arg Glu Arg Lys Ser Ser Ser Ser Ser<br>420 425 430 | 1296 |
| gaa gac agg aat cga atg aaa aca ctt ggt aga cgg gac tcg agt gat<br>Glu Asp Arg Asn Arg Met Lys Thr Leu Gly Arg Arg Asp Ser Ser Asp<br>435 440 445 | 1344 |
| gat tgg gag att cct gat ggg cag att aca gtg gga caa aga att gga<br>Asp Trp Glu Ile Pro Asp Gly Gln Ile Thr Val Gly Gln Arg Ile Gly<br>450 455 460 | 1392 |
| tct gga tca ttt gga aca gtc tac aag gga aag tgg cat ggt gat gtg<br>Ser Gly Ser Phe Gly Thr Val Tyr Lys Gly Lys Trp His Gly Asp Val<br>465 470 475 480 | 1440 |
| gca gtg aaa atg ttg aat gtg aca gca cct aca cct cag cag tta caa<br>Ala Val Lys Met Leu Asn Val Thr Ala Pro Thr Pro Gln Gln Leu Gln<br>485 490 495 | 1488 |
| gcc ttc aaa aat gaa gta gga gta ctc agg aaa aca cga cat gtg aat<br>Ala Phe Lys Asn Glu Val Gly Val Leu Arg Lys Thr Arg His Val Asn<br>500 505 510 | 1536 |
| atc cta ctc ttc atg ggc tat tcc aca aag cca caa ctg gct att gtt<br>Ile Leu Leu Phe Met Gly Tyr Ser Thr Lys Pro Gln Leu Ala Ile Val<br>515 520 525 | 1584 |
| acc cag tgg tgt gag ggc tcc agc ttg tat cac cat ctc cat atc att<br>Thr Gln Trp Cys Glu Gly Ser Ser Leu Tyr His His Leu His Ile Ile<br>530 535 540 | 1632 |
| gag acc aaa ttt gag atg atc aaa ctt ata gat att gca cga cag act<br>Glu Thr Lys Phe Glu Met Ile Lys Leu Ile Asp Ile Ala Arg Gln Thr<br>545 550 555 560 | 1680 |
| gca cag ggc atg gat tac tta cac gcc aag tca atc atc cac aga gac<br>Ala Gln Gly Met Asp Tyr Leu His Ala Lys Ser Ile Ile His Arg Asp<br>565 570 575 | 1728 |
| ctc aag agt aat aat ata ttt ctt cat gaa gac ctc aca gta aaa ata<br>Leu Lys Ser Asn Asn Ile Phe Leu His Glu Asp Leu Thr Val Lys Ile<br>580 585 590 | 1776 |
| ggt gat ttt ggt cta gct aca gtg aaa tct cga tgg agt ggg tcc cat<br>Gly Asp Phe Gly Leu Ala Thr Val Lys Ser Arg Trp Ser Gly Ser His<br>595 600 605 | 1824 |
| cag ttt gaa cag ttg tct gga tcc att ttg tgg atg gca cca gaa gtc<br>Gln Phe Glu Gln Leu Ser Gly Ser Ile Leu Trp Met Ala Pro Glu Val<br>610 615 620 | 1872 |
| atc aga atg caa gat aaa aat cca tac agc ttt cag tca gat gta tat<br>Ile Arg Met Gln Asp Lys Asn Pro Tyr Ser Phe Gln Ser Asp Val Tyr<br>625 630 635 640 | 1920 |
| gca ttt gga att gtt ctg tat gaa ttg atg act gga cag tta cct tat<br>Ala Phe Gly Ile Val Leu Tyr Glu Leu Met Thr Gly Gln Leu Pro Tyr<br>645 650 655 | 1968 |
| tca aac atc aac aac agg gac cag ata att ttt atg gtg gga cga gga<br>Ser Asn Ile Asn Asn Arg Asp Gln Ile Ile Phe Met Val Gly Arg Gly<br>660 665 670 | 2016 |
| tac ctg tct cca gat ctc agt aag gta cgg agt aac tgt cca aaa gcc<br>Tyr Leu Ser Pro Asp Leu Ser Lys Val Arg Ser Asn Cys Pro Lys Ala<br>675 680 685 | 2064 |
| atg aag aga tta atg gca gag tgc ctc aaa aag aaa aga gat gag aga<br>Met Lys Arg Leu Met Ala Glu Cys Leu Lys Lys Lys Arg Asp Glu Arg<br>690 695 700 | 2112 |
| cca ctc ttt ccc caa att ctc gcc tct att gag ctg ctg gcc cgc tca<br>Pro Leu Phe Pro Gln Ile Leu Ala Ser Ile Glu Leu Leu Ala Arg Ser<br>705 710 715 720 | 2160 |

-continued

```
ttg cca aaa att cac cgc agt gca tca gaa ccc tcc ttg aat cgg gct    2208
Leu Pro Lys Ile His Arg Ser Ala Ser Glu Pro Ser Leu Asn Arg Ala
            725                 730                 735 ggt ttc caa aca gag gat ttt agt cta tat gct tgt gct tct cca aaa    2256
Gly Phe Gln Thr Glu Asp Phe Ser Leu Tyr Ala Cys Ala Ser Pro Lys
        740                 745                 750 aca ccc atc cag gca ggg gga tat ggt gcg ttt cct gtc cac tga        2301
Thr Pro Ile Gln Ala Gly Gly Tyr Gly Ala Phe Pro Val His
    755                 760                 765
```

<210> SEQ ID NO 2
<211> LENGTH: 766
<212> TYPE: PRT
<213> ORGANISM: Homo sapiens

<400> SEQUENCE: 2

```
Met Ala Ala Leu Ser Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Ser Pro Ser Ala
305                 310                 315                 320
```

```
Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
                340                 345                 350

His Arg Asn Gln Phe Gly Gln Arg Asp Arg Ser Ser Ala Pro Asn
                355                 360                 365

Val His Ile Asn Thr Ile Glu Pro Val Asn Ile Asp Asp Leu Ile Arg
    370                 375                 380

Asp Gln Gly Phe Arg Gly Asp Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser
                420                 425                 430

Glu Asp Arg Asn Arg Met Lys Thr Leu Gly Arg Arg Asp Ser Ser Asp
                435                 440                 445

Asp Trp Glu Ile Pro Asp Gly Gln Ile Thr Val Gly Gln Arg Ile Gly
                450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
                500                 505                 510

Ile Leu Leu Phe Met Gly Tyr Ser Thr Lys Pro Gln Leu Ala Ile Val
                515                 520                 525

Thr Gln Trp Cys Glu Gly Ser Ser Leu Tyr His His Leu His Ile Ile
                530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
                580                 585                 590

Gly Asp Phe Gly Leu Ala Thr Val Lys Ser Arg Trp Ser Gly Ser His
                595                 600                 605

Gln Phe Glu Gln Leu Ser Gly Ser Ile Leu Trp Met Ala Pro Glu Val
                610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
                660                 665                 670

Tyr Leu Ser Pro Asp Leu Ser Lys Val Arg Ser Asn Cys Pro Lys Ala
                675                 680                 685

Met Lys Arg Leu Met Ala Glu Cys Leu Lys Lys Arg Asp Glu Arg
                690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735
```

-continued

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His
            755                 760                 765

<210> SEQ ID NO 3
<211> LENGTH: 20
<212> TYPE: DNA
<213> ORGANISM: Artificial Sequence
<220> FEATURE:
<223> OTHER INFORMATION: RT-PCR forward primer

<400> SEQUENCE: 3
gggccccggc tctcggttat                                              20

<210> SEQ ID NO 4
<211> LENGTH: 27
<212> TYPE: DNA
<213> ORGANISM: Artificial Sequence
<220> FEATURE:
<223> OTHER INFORMATION: RT-PCR reverse primer

<400> SEQUENCE: 4
tgctactctc ctgaactctc tcactca                                      27

<210> SEQ ID NO 5
<211> LENGTH: 18
<212> TYPE: DNA
<213> ORGANISM: Artificial Sequence
<220> FEATURE:
<223> OTHER INFORMATION: Nested PCR forward primer

<400> SEQUENCE: 5
gttcaacggg gacatgga                                                18

<210> SEQ ID NO 6
<211> LENGTH: 18
<212> TYPE: DNA
<213> ORGANISM: Artificial Sequence
<220> FEATURE:
<223> OTHER INFORMATION: Nested PCR reverse primer

<400> SEQUENCE: 6
atggtgcgtt tcctgtcc                                                18

<210> SEQ ID NO 7
<211> LENGTH: 18
<212> TYPE: DNA
<213> ORGANISM: Artificial Sequence
<220> FEATURE:
<223> OTHER INFORMATION: COLD PCR forward primer

<400> SEQUENCE: 7
actgcacagg gcatggat                                                18

<210> SEQ ID NO 8
<211> LENGTH: 19
<212> TYPE: DNA
<213> ORGANISM: Artificial Sequence
<220> FEATURE:
<223> OTHER INFORMATION: COLD PCR reverse primer

<400> SEQUENCE: 8
tctggtgcca tccacaaaa                                               19

METHODS FOR DETERMINING AND INHIBITING RHEUMATOID ARTHRITIS ASSOCIATED WITH THE BRAF ONCOGENE IN A SUBJECT

This patent application claims the benefit of the filing date of U.S. Ser. No. 61/472,119, filed Apr. 5, 2011, the contents of all of which are herein incorporated by reference in their entireties into the present patent application.

Throughout this application various publications are referenced. The disclosures of these publications in their entireties are hereby incorporated by reference into this application in order to more fully describe the state of the art to which this invention pertains.

BACKGROUND OF THE INVENTION

Synovial fibroblasts destroy articular cartilage and bone in rheumatoid arthritis, but the mechanism of fibroblast transformation remains elusive. Since gain-of-function mutations of BRAF can transform fibroblasts, we examined BRAF in rheumatoid synovial fibroblasts. The strong gain-of-function mutation, V600R, of BRAF found in melanomas and other cancers was identified in first passage synovial fibroblasts from two of nine RA patients and confirmed by restriction site mapping. BRAF-specific siRNA inhibited proliferation of synovial fibroblasts with V600R mutations. A BRAF aberrant splice variant with an intact kinase domain and partial loss of the N-terminal autoinhibitory domain was identified in fibroblasts from an additional patient, and fibroblast proliferation was inhibited by BRAF-specific siRNA. Our finding is the first to establish mechanisms for fibroblast transformation responsible for destruction of articular cartilage and bone in rheumatoid arthritis and establishes a new target for therapeutic intervention.

Rheumatoid arthritis (RA) is a chronic inflammatory disease that occurs in 1% of the population and is characterized by progressive erosive arthritis of multiple joints associated with increased mortality. Although the inflammatory reaction contains numerous cell types, synovial fibroblasts have been identified as the cell responsible for invasion and destruction of cartilage and bone (Muller-Ladner, U., et al. (1996) *Am J Pathol,* 149, 1607-1615; Pap, T., et al. (2000) *Arthritis Res,* 2, 361-367; Buckley, C. D., et al. (2001) *Trends Immunol,* 22, 199-204; Muller-Ladner, U., et al. (2005) *Nat Clin Pract Rheumatol,* 1, 102-110; Pap, T., et al. (2005) *Ann Rheum Dis,* 64 Suppl 4, iv52-54; Karouzakis, E., et al. (2006) *Immunol Lett,* 106, 8-13; Huber, L. C., et al. (2006) *Rheumatology* (Oxford), 45, 669-675). Rheumatoid synovial fibroblasts show evidence of transformation indicated by excessive proliferation, loss of contact inhibition, and increased migration (Pap, T., et al. (2000) *Arthritis Res,* 2, 361-367; Karouzakis, E., et al. (2006) *Immunol Lett,* 106, 8-13; Mercer, K., et al. (2005) *Cancer Res,* 65, 11493-11500). Transformation of RA synovial fibroblasts has also been demonstrated in an animal model of RA employing xenograft implants of RA synovium as evidenced by metastasis of implanted synovial fibroblasts with localization and binding to cartilage (Lefevre, S., et al. (2009) *Nat Med,* 15, 1414-1420). The mechanism of RA synovial fibroblast transformation has not been identified, but it is critical for the rational design of therapies to prevent joint destruction. In spite of evidence for neoplastic transformation of RA synovial fibroblasts, oncogenes potentially responsible for transformation have not been identified. Since gain-of-function mutations in the BRAF oncogene have been shown to transform embryonic fibroblasts but not several other somatic cell types, we examined rheumatoid synovial fibroblasts for the presence of BRAF mutations (Mercer, K., et al. (2005) *Cancer Res,* 65, 11493-11500).

SUMMARY OF THE INVENTION

The invention provides methods for determining or diagnosing whether a subject is suffering from a rheumatoid arthritis (RA) associated with the BRAF oncogene. In one embodiment, the method comprises contacting isolated fibroblasts from the subject with a molecule or pool of molecules directed to the BRAF oncogene. The method further comprises detecting association of the agent with the BRAF oncogene, e.g. such that BRAF oncogene expression is decreased and fibroblasts return to a less transformed phenotype, decreased cell proliferation and increased contact inhibition, being indicative that the subject is suffering from a rheumatoid arthritis associated with the BRAF oncogene.

The invention additionally provides methods for inhibiting cells having a mutant BRAF associated with RA and methods for treating subjects having RA associated with the BRAF oncogene.

The invention further provides methods for identifying molecules that bind or block the BRAF protein in a rheumatoid arthritis cell. The method comprises contacting a molecule of interest with the BRAF protein. The method also comprises determining whether the molecule of interest alters BRAF protein activity, alteration of the BRAF protein activity being indicative that the molecule of interest binds or blocks the BRAF protein in the cell.

Additionally provided are compositions containing one or more agents that bind or block BRAF for inhibiting RA.

BRIEF DESCRIPTION OF THE FIGURES

FIG. 1A. Loss of fibroblast contact inhibition. Rheumatoid synovial fibroblasts were grown in T25 flasks and observed microscopically. Fibroblast transformation is suggested by the loss of contact inhibition. A representative example is shown. Bar, 20 µm. FIG. 1B. BRAF amplified by RT and nested PCR. Nested PCR amplified a DNA fragment of about 2300 bp in all patients. DNA sequencing confirmed the presence of BRAF. Aberrant splice variants were observed in RA6, RA8, and RA9 as confirmed by DNA sequencing. FIG. 1C. Splice variants of BRAF from rheumatoid synovial fibroblasts. Shown are the deletion of exons in splice variants from RA6, RA8, and RA9. RA8 has a splice variant that deletes a portion of the BRAF autoinhibitory domain but retains the kinase domain.

FIG. 3A. The SfcI restriction site includes the first nucleotide of the codon for BRAF residue 600. FIG. 3B. Incomplete SfcI digestion of 2300 bp BRAF cDNA obtained by PCR (inverted image) is consistent with V600R of BRAF from RA6. In contrast, 2300 bp BRAF cDNA from RA3 without BRAF mutation shows complete digestion by SfcI. FIG. 3C. Incomplete SfcI digestion of 191 bp BRAF cDNA fragment obtain by "Fast COLD PCR" (inverted image) is consistent with V600R of BRAF from RA1. In contrast, 191 bp BRAF cDNA from RA3 without BRAF mutation shows complete digestion by SfcI. Arrows indicate uncleaved cDNA following digestion with excess SfcI.

FIG. 4A. Synovial fibroblasts from 5 RA patients and 1 OA patient were cultured for 72 hours in the presence of control and BRAF-specific siRNA. Significant inhibition of growth in response to BRAF siRNA was observed in fibroblasts from RA1 and RA6 with a V600R mutation of BRAF and in RA8 with a BRAF splice variant containing a partial deletion of the autoinhibitory domain. FIG. 4B. BRAF siRNA inhibits production of BRAF. Synovial fibroblasts from RA6 were incubated with BRAF siRNA for 72 hours and assessed for BRAF production by Western blot. Actin served as a loading control:

FIG. 5A. Synovial tissue was obtained from patients with rheumatoid arthritis undergoing joint-replacement surgery. Synovial tissue was treated with collagenase, and cell suspensions were cultured in DMEM/F12 (1:1) medium containing 10% FCS. RNA was isolated from pure fibroblast cultures, and cDNA was produced with BRAF-specific primers outside of the coding sequence by RT-PCR. Nested PCR was performed with BRAF-specific primers within the coding sequence. Aberrant splice variants were identified by direct nucleotide sequencing of gel-purified DNA. FIG. 5B. Direct sequencing of gel-purified DNA showed aberrant BRAF splice variants characterized by exon skipping. Shown are deleted exons of BRAF.

FIG. 6. RNA was isolated from rheumatoid synovial fibroblasts, and KRAS cDNA was obtained by RT-PCR with KRAS-specific primers located in the non-coding sequence. Nested PCR was then performed with KRAS-specific primers located within the coding sequence. PCR fragments were then ligated into PCR2.1 for DNA sequencing. KRAS mutants were identified in synovial fibroblasts from 7 of 9 patients.

DETAILED DESCRIPTION OF THE INVENTION

Definitions

Figure 1:
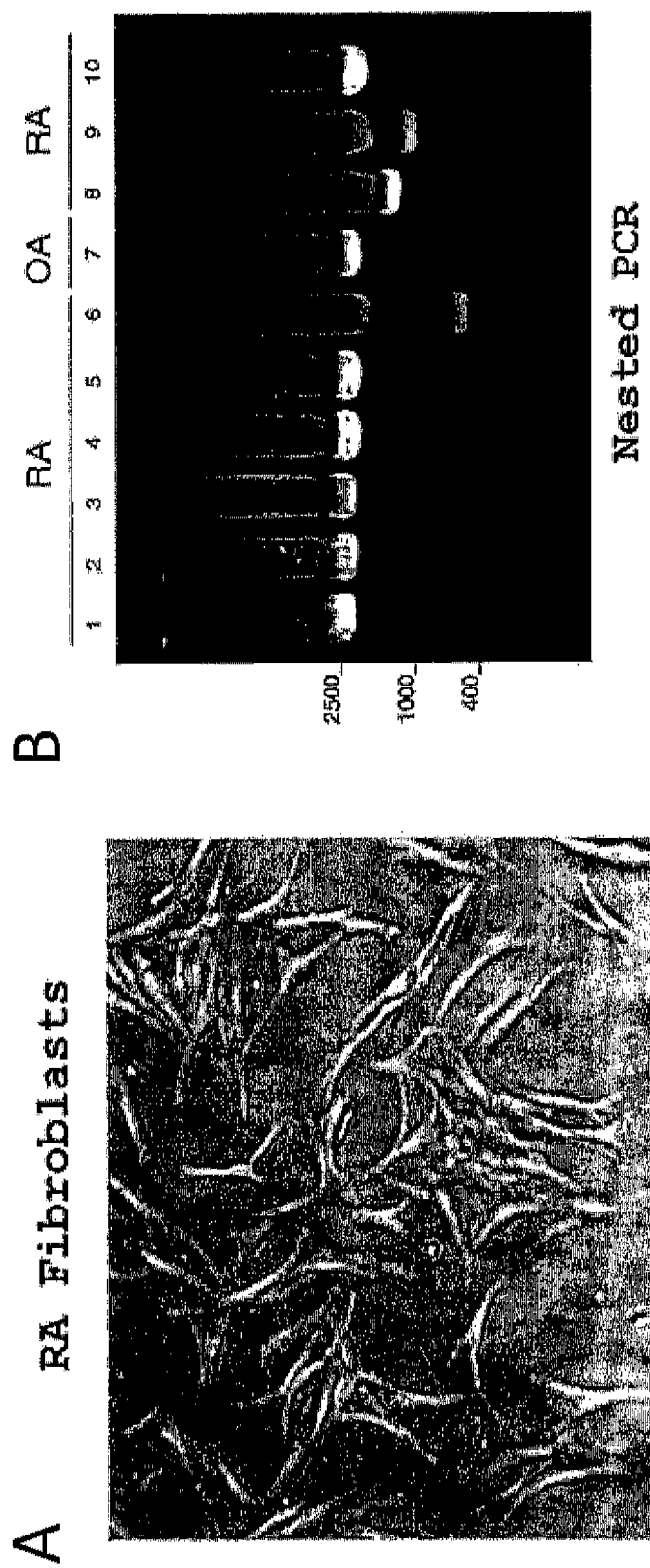
FIGS. 1A-1C. PCR amplification of BRAF from RA fibroblasts.
Figure 1:
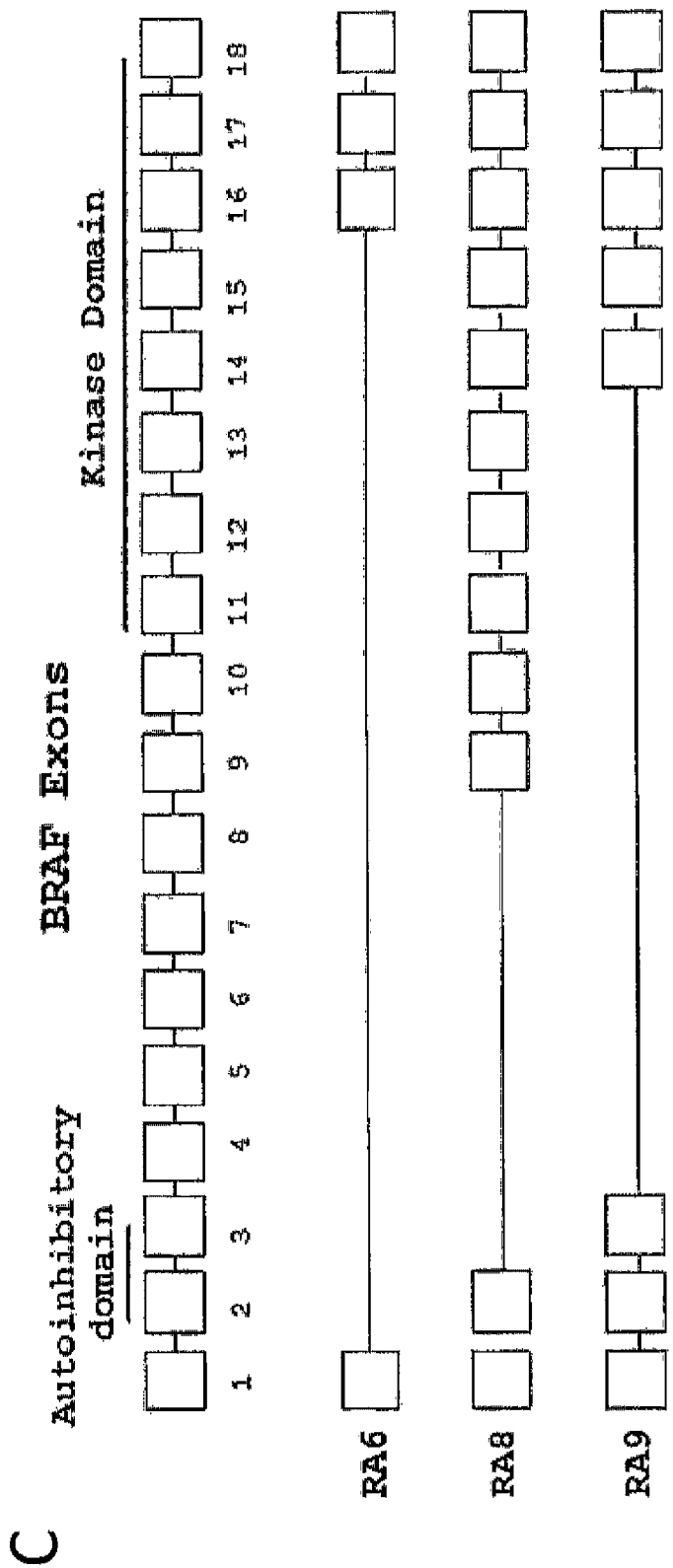

Unless defined otherwise, all technical and scientific terms used herein have the same meaning as is commonly understood by one of ordinary skill in the art to which this invention belongs. All patents, applications, published applications and other publications referred to herein are incorporated by reference in their entirety.

The term "BRAF oncogene" includes nucleic acid sequences containing one or more additions, deletions or substitutions relative to the BRAF oncogene described herein, e.g., SEQ ID NO:1 and BRAF oncogenes from humans and other species. In addition, the term "BRAF oncogene" includes RNA transcripts containing all or a portion of the nucleic acid sequence described in SEQ ID NO: 1, as well as the genomic sequences corresponding to the SEQ ID NO:1 along with its transcripts and the associated introns, exons, untranslated leader region, splice donors, splice acceptors, polyadenylation signals, promoter, and transcriptional enhancers, as may be found in publically available sequence, bibliological, and journal article databases, such as but not limited to those housed at the National Center for Biotechnology Information, Bethesda, Md. (web address: www.ncbi.nlm.nih.gov) and HUGO Gene Nomenclature Committee, Cambridge, UK (http://www.genenames.org) and their associated web links. Another name for "BRAF" is "v-raf murine sarcoma viral oncogene homolog B1."

The term "BRAF protein" includes proteins encoded by the nucleic acid sequence provided in SEQ ID NO:1 and may contain one or more additions, deletions or substitutions relative to the wild-type as given in SEQ ID NO:2 and includes the variants described herein. Furthermore, the term "BRAF protein" includes BRAF proteins from humans and other species.

The phrase "mutant or variant BRAF or aberrant BRAF splice variants" refers to a BRAF oncogene that can be processed or spliced, by one or more processing reactions, to produce mutant or variant BRAF or aberrant BRAF splice variants. BRAF variants may generally contain either a deletion (part or whole) of a RAS-binding domain (RBD) at exons 3-5 (including anywhere between exons 3-5) or a deletion (partial or whole) of the RBD and the kinase domain (e.g., at exons 11-17 (including any change that would eliminate the kinase activity of the oncogene)). Additionally, the change may include mutations that results in BRAF proteins that exhibit gain-of-function. The gain-of-function mutation includes point mutations such as that affecting valine at amino acid 600 or deletions of the BRAF protein.

The source of BRAF can be a live organism (including a human patient, or a laboratory or veterinary animal, such as dog, pig, cow, horse, rat or mice), a sample therefrom (such as a tissue or body fluid, or extract thereof), a cell (such as a primary cell or cell line, or extract thereof), extracellular medium or matrix or milieu, or isolated protein.

The phrase "inhibit" or "inhibiting" with respect to cells (e.g. fibroblasts) associated with rheumatoid arthritis (RA) having the BRAF oncogene, refers to any one or more of a detectable inhibition of the growth of cells (e.g. fibroblasts) (in or from the subject); BRAF oncogene expression is increased; cells (e.g. fibroblasts) return to a more transformed phenotype; and decreased contact inhibition by the cells (e.g. fibroblasts). Inhibiting cells (e.g. fibroblasts) associated with RA having the BRAF oncogene can be evidenced, for example, by a decrease of at least 5%, such as at least 10%, 20%, 30%, 40%, 50%, 75%, 90% or more, of the number, or relative number, of cells (e.g. fibroblasts), relative to a reference level. Inhibition can be a decrease that is a statistically significant difference relative to the reference level.

The phrase "contacting or exposing" refers to bringing into association, either directly or indirectly, two or more substances. Contacting may occur in vivo, ex vivo or in vitro. For example, a source of BRAF e.g., a cell or tissue, that is a human or other animal may be contacted with an agent (e.g., a molecule (such as nucleic acid molecules), compound or antibody including fragments thereof), for example, by therapeutic or prophylactic administration of the agent. A source of BRAF that is a fluid, such as extracellular medium, can be contacted with an agent, for example, by admixing the agent with the fluid.

The phrase "treating" or "treatment" refers to any manner in which one or more of the symptoms of a disease or disorder (such as RA) are ameliorated or otherwise beneficially altered, whether in a permanent or temporary manner, which can be attributed to or associated with administration of the agent or composition herein. The term encompasses any pharmaceutical use, including prophylactic uses in which the development of one or more of the symptoms of a disease or disorder (e.g., RA) is prevented, delayed or reduced, whether in a permanent or temporary manner, which can be attributed to or associated with administration of the composition.

Methods of the Invention

The present invention provides methods for determining or diagnosing whether a subject is suffering from a rheumatoid arthritis associated with the BRAF oncogene.

In an embodiment of the invention, the method comprising contacting a sample from the subject with an agent (e.g. a molecule or pool of molecules) directed to the BRAF oncogene or its transcript(s). The method further comprises detecting association of the agent with the BRAF oncogene or its transcript(s) (e.g., by detecting a complex between the BRAF oncogene or its transcript(s) and the agent). The association may be indicative that the subject is suffering from a rheumatoid arthritis associated with the BRAF oncogene. In an embodiment of the invention, the BRAF oncogene has a mutation so that the codon encoding valine at nucleotide position 1798-1800 of SEQ ID NO:1 is changed to any of the codons CGU, CGC, CGA, CGG, AGA, and AGG which encodes arginine.

In another embodiment, the method comprises contacting a sample from the subject with an agent or agents directed to different portions of the BRAF oncogene; and detecting the association or lack of association of the agent or agents with different portions of the BRAF oncogene. Further, the method provides quantifying the amount of association to different portions of the BRAF oncogene. In this embodiment, the changes in the amount of association affecting one or more portion(s) of the BRAF oncogene but not other(s) is indicative that the subject is suffering from a rheumatoid arthritis associated with the BRAF oncogene. Further, in this embodiment, the BRAF oncogene is a mutant BRAF oncogene.

In a further embodiment, the method comprises (a) contacting or exposing a sample (e.g. isolated fibroblasts) from the subject (e.g., a subject suffering from rheumatoid arthritis) with an agent (e.g. a molecule or pool of molecules) directed to the BRAF oncogene. Further, the method comprising detecting association of the agent with the BRAF oncogene in the sample such that (1) BRAF oncogene expression is decreased, (2) fibroblasts return to a less transformed phenotype, and/or (3) fibroblasts exhibit decreased cell proliferation and/or increased contact inhibition, one or more of these features being indicative that the subject is suffering from a rheumatoid arthritis associated with the BRAF oncogene.

In another embodiment, the method comprises contacting a sample from the subject with an agent (e.g., a molecule or pool of molecules) directed to the BRAF oncogene. Further, the method comprises culturing the sample in the presence of the molecule or pool of molecules and determining whether BRAF oncogene expression by the cell is decreased and/or whether cells in the sample return to a less transformed phenotype, exhibit decreased cell proliferation and/or exhibit increased contact inhibition, any of which is indicative that the subject is suffering from a rheumatoid arthritis associated with the BRAF oncogene.

In accordance with the practice of the invention, the molecule that is directed to or binds the BRAF oncogene may be a nucleic acid molecule. In one embodiment, the nucleic acid molecule may be a RNA molecule, and the RNA molecule is a siRNA molecule. Additionally, the nucleic acid molecule may be an antisense molecule. In a further embodiment, the siRNA or antisense molecule is directed to the BRAF oncogene sequence.

In an embodiment of the invention, the sample is a cell sample, a biological fluid sample (e.g., synovial fluid) or tissue sample.

In one embodiment, the sample includes fibroblasts, e.g., fibroblasts isolated from synovial tissue or fluid from the subject.

In another embodiment, the BRAF oncogene comprises one or more nucleic acid mutations in nucleotide position 1798 to nucleotide position 1800 of SEQ ID NO:1. For example, in one embodiment, the mutation results in a BRAF protein, wherein valine at amino acid position 600 of SEQ ID NO:2 is changed to an amino acid other than valine (such as alanine, arginine, asparagine, aspartic acid, cysteine, glutamine, glutamic acid, glycine, histidine, isoleucine, leucine, lysine, methionine, phenylalanine, proline, serine, threonine, tryptophan, and tyrosine). In a preferred embodiment, the mutation at amino acid position 600 of SEQ ID NO:2 is a change from valine to arginine (V600R). The V600R change involves replacing the codon GTG (at nucleotide positions 1798-1800 of SEQ ID NO:1) which encodes valine with any of the codons CGU, CGC, CGA, COG, AGA, and AGG which encodes arginine.

In a further embodiment, the BRAF oncogene is analyzed for a mutation or mutations in codon 600 by reverse transcribing RNA isolated from the fibroblasts from synovial tissue of the subject so as to obtain cDNA. The BRAF oncogene may be analyzed for a mutation or mutations in codon 600 also by amplifying the cDNA so obtained and determining whether the BRAF oncogene at codon 600 is mutated such that codon 600 valine is replaced with an amino acid other than valine (e.g. arginine).

In another embodiment, the BRAF oncogene encodes a BRAF protein as shown in SEQ ID NO:2 beginning with methionine at amino position 1 and ending with histidine at amino acid position 766. In this embodiment, the BRAF oncogene begins with adenosine at nucleotide position 1 and ends with cytosine at nucleotide position 2298 of SEQ ID NO:1.

In an embodiment of the invention, the BRAF oncogene encodes a BRAF protein having an auto-inhibitory domain which has an amino acid sequence beginning at position 47 through position 245 of SEQ ID NO:1 encoded by a nucleic acid sequence beginning with nucleotide position 139 and ending with nucleotide position 735 of SEQ ID NO:1, respectively, and a kinase domain which has an amino acid sequence beginning at position 433 and ending with position 726 of SEQ ID NO:1 which is encoded by a nucleic acid sequence beginning with nucleotide position 1297 and ending with nucleotide position 2178 of SEQ ID NO:1, respectively.

In a further embodiment, the BRAF oncogene encodes a mutant BRAF protein wherein the auto-inhibitory domain of the BRAF protein is deleted, e.g., entirely or partially. In one example, the kinase domain is intact or remains unchanged and is functional (i.e., retains its catalytic function) and/or is constitutively active, the latter, a gain-of-function mutation or activating mutation within the kinase domain. In another example, the kinase domain is changed (e.g., by mutating one of more amino acids within position 433 through position 726 of SEQ ID NO:1) but the kinase domain remains functional and/or is constitutively active, the latter, a gain-of-function mutation or activating mutation within the kinase domain.

In an additional embodiment, the BRAF protein is a mutant BRAF protein of SEQ ID NO:1 wherein the auto-inhibitory domain of the BRAF protein beginning with amino acid at position 47 and ending with amino acid at position 245 (which is encoded by nucleic acid sequence beginning at nucleotide position 139 and ending with nucleotide position 735 of SEQ ID NO:1), is deleted, entirely or partially, but the kinase domain beginning with amino acid at position 433 and ending with amino acid position 726 of SEQ ID NO:2 (which is encoded by nucleic acid sequence beginning at nucleotide position 1297 and ending with nucleotide position 2178 of SEQ ID NO:1), is intact or may be altered at one or more nucleic acid or amino acid position but remains functional as a kinase domain (e.g., such as that exhibited by the kinase domain of unaltered BRAF oncogene).

In another embodiment, the BRAF oncogene is a mutant BRAF oncogene (e.g. so that it is an alternatively spliced BRAF transcript as shown in SEQ ID NO:1) which is missing exons 3-8 beginning with nucleotide position 241 through nucleotide position 1140 of SEQ ID NO:1 and encodes a mutant (e.g., truncated) BRAF protein that is missing an amino acid sequence beginning with amino acid position 81 to amino acid position 380 of SEQ ID NO:1.

In a further embodiment, the BRAF oncogene is an alternatively spliced BRAF transcript as shown in SEQ ID NO:1 which is missing the nucleic acid sequence beginning at nucleotide position 505 to nucleotide position 1992 so that it encodes a mutant BRAF protein shown in SEQ ID NO:1 but which is missing an amino acid sequence beginning at amino acid position 169 through amino acid position 664.

In a yet further embodiment, wherein the BRAF oncogene is an alternatively spliced BRAF transcript as shown in SEQ ID NO:1 which is missing the nucleic acid sequence beginning at nucleotide position 139 to nucleotide position 1992 so that it encodes a mutant BRAF protein shown in SEQ ID NO:1 but which is missing an amino acid sequence beginning at amino acid position 47 through amino acid position 664.

In a still further embodiment, the BRAF oncogene is an alternatively spliced BRAF transcript as shown in SEQ ID NO:1 which is missing the nucleic acid sequence beginning at nucleotide position 139 to nucleotide position 1860 so that it encodes a mutant BRAF protein shown in SEQ ID NO:1 but which is missing an amino acid sequence beginning at amino acid position 47 through amino acid position 620.

In an additional embodiment, the BRAF oncogene is an alternatively spliced BRAF transcript as shown in SEQ ID NO:1 which is missing the nucleic acid sequence beginning at nucleotide position 505 to nucleotide position 1695 so that it encodes a mutant BRAF protein shown in SEQ ID NO:1 but which is missing amino acid sequence beginning at amino acid position 169 and ending at amino acid position 565.

The invention additionally provides methods for determining whether a subject is suffering from a rheumatoid arthritis which is associated with either a mutant BRAF oncogene or an aberrant activation of the RAS-ERK-MAPK signaling pathway or both. In one embodiment, the method comprises determining whether the subject is suffering a rheumatoid arthritis associated with a mutant BRAF oncogene by a method described above. The method also comprises determining whether the subject is suffering from a aberrant activation of the RAS-ERK-MAPK signaling pathway for example by isolating nucleic acid sequence of each component of the signaling pathway from the sample; determining the nucleic acid sequence and comparing it to the wild-type nucleic acid sequence to identify presence of a mutation(s) in the coding region; expressing the mutant protein in a mammalian cell so as to be able to determine its activity relative to the non-mutant or wild-type protein, similarly expressed; and determining the phosphorylation state of different components of the signaling pathway, such that an increase in the phosphorylation state observed with the mutant protein relative to the non-mutant or wild-type protein being indicative of a subject suffering from a rheumatoid arthritis associated with aberrant activation of the signaling pathway.

In accordance with the practice of the invention, a component of the signaling pathway includes HRAS, NRAS, KRAS, ARAF, BRAF, CRAF, MEK1, MEK2, ERK1 and ERK2 coding sequences.

Further, in accordance with the practice of the invention, the sample may be a cell sample, a biological fluid sample (e.g., synovial fluid) or tissue sample. The sample contains fibroblasts such as fibroblasts.

In an embodiment of the invention, the coding sequence for the mutant or wild-type protein is expressed in a mammalian cell through the use of a mammalian expression system either inducible or constitutively, following introduction of the mammalian expression system along with the coding sequences of interest into the mammalian cell. Examples of mammalian cells include COS-7 cell, HEK-293 cell, U2OS cell, and HeLa.

In an embodiment of the invention, the phosphorylation state of HRAS, NRAS, KRAS, ARAF, BRAF, CRAF, MEK1, MEK2, ERK1 or ERK2 protein may be determined with a phospho-specific antibody.

The invention additionally provides methods for inhibiting cells having an activated BRAF oncogene associated with rheumatoid arthritis. In one embodiment, the method comprises contacting the cells with an agent that binds the BRAF oncogene and thereby inhibiting the cells.

The invention additionally provides methods for treating a subject suffering from rheumatoid arthritis associated with a BRAF oncogene. In one embodiment, the method comprises administering an agent molecule that binds the BRAF protein to the subject suffering from a rheumatoid arthritis associated with the BRAF oncogene and thereby treating the subject suffering from rheumatoid arthritis.

In accordance with the practice of the invention, the agent may be administered in or around a joint area of the subject such as in the joint area of the knee, ankle, elbow, hand, shoulder, or hip.

Also, in one embodiment, the agent that binds the BRAF protein is a BRAF inhibitor. In accordance with the practice of the invention, the BRAF inhibitor may be administered alone or in combination (concurrent or sequential) with one or more medications for rheumatoid arthritis (e.g., immunosuppression agents).

Examples of immunosuppressive agents include methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE®), etanercept, TNFα, blockers, a biological agent that targets an inflammatory cytokine, and, Nonsteroidal Anti-inflammatory Drugs (NSAIDS). NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

Examples of suitable BRAF inhibitors include but are not limited to PLX4032 (also known as N-(3-(5-(4-chlorophenyl)-1H-pyrrolo[2,3-b]pyridine-3-carbonyl)-2,4-difluorophenyl)propane-1-sulfonamide) (Plexxikon, Inc., Berkeley, Calif.; (24)), RAF265 (also known as 1-methyl-5-(2-(4-(trifluoromethyl)-1H-imidazol-2-yl)pyridin-4-yloxy)-N-(4-(trifluoromethyl)phenyl)-1H-benzo[d]imidazol-2-amine) (CHIR-265; Novartis Pharmaceuticals, Basel, Switzerland), Sorafenib (also known as 4-[4-[[4-chloro-3-(trifluoromethyl)

phenyl]carbamoylamino]phenoxy]-N-methyl-pyridine-2-carboxamide) (BAY43-9006; Bayer, Pittsburgh, Pa.), XL281 (Exelixis, San Francisco, Calif.), SB-590885 (also known as 5-[2-[4-[2-(Dimethylamino) ethoxy]phenyl]-5-(4-pyridinyl)-1H-imidazol-4-yl]-2,3-dihydro-1H-inden-1-oneoxime) (SmithKline Beecham, Philadelphia, Pa.), and PLX4720 (also known as N-(3-(5-chloro-1H-pyrrolo[2,3-b]pyridine-3-carbonyl)-2,4-difluorophenyl)propane-1-sulfonamide) (Plexxikon, Inc., Berkeley, Calif.).

In another embodiment, the method for treating a subject suffering from rheumatoid arthritis associated with a BRAF oncogene comprises administering a molecule that targets the BRAF oncogene or transcripts thereof in the subject and thereby treating the subject suffering from rheumatoid arthritis.

In accordance with the practice of the invention, the molecule that targets the BRAF oncogene or transcripts thereof may be a nucleic acid molecule. For example, the nucleic acid molecule may be a RNA molecule such as a siRNA molecule. In one embodiment, the siRNA molecule is directed to the BRAF oncogene sequence.

In another embodiment, the method for treating a subject suffering from rheumatoid arthritis associated with the BRAF oncogene comprises administering an agent (e.g., a molecule) that inhibits the RAS-RAF-MAPK signaling pathway to the subject suffering from a rheumatoid arthritis associated with the BRAF oncogene and thereby treating the subject suffering from rheumatoid arthritis.

In an embodiment, the agent that inhibits the RAS-RAF-MAPK signaling pathway is a MEK inhibitor or an ERK inhibitor. Suitable examples of MEK inhibitors include but are not limited to AZD6244 (also known as 6-(4-bromo-2-chloroanilino)-7-fluoro-N-(2-hydroxyethoxy)-3-methylbenzimidazole-5-carboxamide) (ARMY-142886; AstraZeneca, London, England), PD0325901 (also known as (R)—N-(2,3-dihydroxypropoxy)-3,4-difluoro-2-((2-fluoro-4-iodophenyl)amino)benzamide), CI-1040 (also known as 2-(2-Chloro-4-iodophenylamino)-N-(cyclopropylmethoxy)-3,4-difluorobenzamide), and XL518 (also known as (S)-(3,4-difluoro-2-((2-fluoro-4-iodophenyl)amino)phenyl)(3-hydroxy-3-(piperidin-2-yl)cyclobutyl)methanone) (Exelixis, San Francisco, Calif.).

Suitable examples of ERK inhibitors include but are not limited to FR180204 (also known as 5-(2-Phenyl-pyrazolo[1,5-a]pyridin-3-yl)-1H-pyrazolo[3,4-c]pyridazin-3-ylamine) (EMD4Biosciences, Merck KGaA, Darmstadt, Germany), CAY10561 (also known as N-[1-(3-chloro-4-fluorophenyl)-2-hydroxyethyl]-4-[4-(3-chlorophenyl)-1H-pyrazol-3-yl]-1H-pyrrole-2-carboxamide) (Cayman Chemical, Ann Arbor, Mich.) and 328006 (also known as 3-(2-Aminoethyl)-5-(4-ethoxyphenyl)methylene)-2,4-thiazolidinedione) (Merck KGaA, Darmstadt, Germany).

The amount of an agent administered to a subject varies depending on several factors including the efficacy of the drug on a specific subject and the toxicity (i.e. the tolerability) of a drug to a specific subject.

In one embodiment, the agent may be administered to the subject with an immunosuppressive agent (concurrently or sequentially). In another embodiment, the agent may be administered before or after administration of the suppressive agent.

Screening Assays

The invention further provides a method of identifying or screening molecules that bind or block the BRAF protein in a rheumatoid arthritis cell comprising contacting a molecule of interest with the BRAF protein, and determining whether the molecule of interest alters BRAF protein activity, alteration of the BRAF protein activity being indicative that the molecule of interest binds or blocks the BRAF protein in the cell.

Compositions of the Invention

The present invention relates to compositions comprising an immunosuppressive agent and a BRAF inhibitor that bind and/or are directed to the BRAF oncogene or proteins. In accordance with the invention, the composition may further comprise an agent that inhibits the RAS-RAF-MAPK signaling pathway such as MEK inhibitor or an ERK inhibitor.

In one embodiment, the BRAF inhibitor may be a nucleic acid molecule, e.g. a RNA molecule such as a siRNA molecule.

The invention also relates to BRAF inhibitor molecules or agents of the invention that bind a portion of a BRAF protein as shown in SEQ ID NO:1 beginning with methionine at nucleotide position 1 and ending with histidine at nucleotide position 2298.

In one embodiment, the molecule or agent may be a protein or polypeptide such as an antibody or fragment thereof that binds a BRAF protein. For example, an antibody that specifically binds the BRAF protein at its C-terminus (e.g., the portion encoded by exon 18 as shown in SEQ ID NO:1). Antibodies again BRAF are well known. Examples include LS-C97196, LS-B1627, LS-B3862, LS-B3444, and LS-C49616 (all from Lsbio.com). Antibodies against a BRAF protein at its C-terminus are well known (Clampi et al. *J. Clin Invest.* 115:94-101 (2005); Lsbio.com). The antibody may be polyclonal, monoclonal, chimeric, or humanized. The antibody may be a full length antibody or may be a fragment of an antibody such as a Fab molecule or F(ab')$_2$ molecule. Another antibody fragment can have as the variable region, an Fv or single chain Fv configuration.

In a further embodiment, the agent may bind to a portion of a BRAF protein wherein the auto-inhibitory domain of the BRAF protein beginning with nucleotide position 139 at amino acid position 47 and ending with nucleotide position 735 at amino acid position 245 of SEQ ID NO:1 is deleted, entirely or partially, but the kinase domain beginning with nucleotide position 1297 at amino acid position 433 and ending with nucleotide position 2178 at amino acid position 726 of SEQ ID NO:1 is intact or remains functional. Examples of immunosuppressive agents include methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE®), etanercept, TNFα blockers, a biological agent that targets an inflammatory cytokine, and, Nonsteroidal Anti-inflammatory Drugs (NSAIDS). NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

Examples of suitable BRAF inhibitors include but are not limited to PLX4032 (also known as N-(3-(5-(4-chlorophenyl)-1H-pyrrolo[2,3-b]pyridine-3-carbonyl)-2,4-difluorophenyl)propane-1-sulfonamide) (Plexxikon, Inc., Berkeley, Calif.; (24)), RAF265 (also known as 1-methyl-5-(2-(4-(trifluoromethyl)-1H-imidazol-2-yl)pyridin-4-yloxy)-N-(4-(trifluoromethyl)phenyl)-1H-benzo[d]imidazol-2-amine) (CHIR-265; Novartis Pharmaceuticals, Basel, Switzerland), Sorafenib (also known as 4-[4-[[4-chloro-3-(trifluoromethyl) phenyl]carbamoylamino]phenoxy]-N-methyl-pyridine-2-carboxamide) (BAY43-9006; Bayer, Pittsburgh, Pa.), XL281 (Exelixis, San Francisco, Calif.), SB-590885 (also known as 5-[2-[4-[2-(Dimethylamino)ethoxy]phenyl]-5-(4-pyridinyl)-1H-imidazol-4-yl]-2,3-dihydro-1H-inden-1-oneoxime) (SmithKline Beecham, Philadelphia, Pa.), and PLX4720 (also known as N-(3-(5-chloro-1H-pyrrolo[2,3-b]pyridine-3-carbonyl)-2,4-difluorophenyl)propane-1-sulfonamide) (Plexxikon, Inc., Berkeley, Calif.).

Suitable examples of MEK inhibitors include but are not limited to AZD6244 (also known as 6-(4-bromo-2-chloroanilino)-7-fluoro-N-(2-hydroxyethoxy)-3-methylbenzimidazole-5-carboxamide) (ARRY-142886; AstraZeneca, London, England), PD0325901 (also known as (R)—N-(2,3-dihydroxypropoxy)-3,4-difluoro-2-((2-fluoro-4-iodophenyl)amino)benzamide), CI-1040 (also known as 2-(2-Chloro-4-iodophenylamino)-N-(cyclopropylmethoxy)-3,4-difluorobenzamide), and XL518 (also known as (S)-(3,4-difluoro-2-((2-fluoro-4-iodophenyl)amino)phenyl)(3-hydroxy-3-(piperidin-2-yl)cyclobutyl)methanone) (Exelixis, San Francisco, Calif.).

Suitable examples of ERK inhibitors include but are not limited to FR180204 (also known as 5-(2-Phenyl-pyrazolo[1,5-a]pyridin-3-yl)-1H-pyrazolo[3,4-c]pyridazin-3-ylamine) (EMD4Biosciences, Merck KGaA, Darmstadt, Germany), CAY10561 (also known as N-[1-(3-chloro-4-fluorophenyl)-2-hydroxyethyl]-4-[4-(3-chlorophenyl)-1H-pyrazol-3-yl]-1H-pyrrole-2-carboxamide) (Cayman Chemical, Ann Arbor, Mich.) and 328006 (also known as 3-(2-Aminoethyl)-5-(4-ethoxyphenyl)methylene)-2,4-thiazolidinedione) (Merck KGaA, Darmstadt, Germany).

A. Compositions for Oral Administration

Oral pharmaceutical dosage forms are either solid, gel or liquid. The solid dosage forms may be tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

1. Solid Compositions for Oral Administration

In certain embodiments, the compositions are solid dosage forms, in one embodiment, capsules or tablets. The tablets, pills, capsules, troches and the like can contain one or more of the following ingredients, or components of the composition of a similar nature:

a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyinylpyrrolidine, povidone, crospovidones, sucrose and starch paste. Lubricants include talc, starch, magnesium or calcium stearate, *lycopodium* and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammuoniated shellac and cellulose acetate phthalates. Film coatings include hydroxyethylcellulose, sodium carboxymethylcellulose, polyethylene glycol 4000 and cellulose acetate phthalate.

The components of the composition could be provided in a form that protects it from the acidic environment of the stomach. For example, the composition can be formulated in an enteric coating that maintains its integrity in the stomach and releases the active components of the composition in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The composition can also be administered as a component of an elixir, suspension, syrup, wafer, sprinkle, chewing gum or the like. A syrup may contain, in addition to the active components of the composition, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is an agent or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous-liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active components of the composition or salt in vegetable oils, glycols, triglycerides, propylene glycol esters (e.g., propylene carbonate) and other such carriers, and encapsulating these solutions or suspensions in hard or soft gelatin capsule shells. Briefly, such formulations include, but are not limited to, those containing components of the composition provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained is also contemplated herein. Briefly, components of the composition provided herein may be dispersed e.g., in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The components of the composition diffuse through the outer polymeric membrane in a release rate controlling step. The percentage of active components of the composition is highly dependent on the specific nature thereof, as well as the activity of the components of the composition and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN™ 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active components of the composition is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing active components of the composition is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active components of the composition to the treated tissue(s).

The components of the composition may be suspended in micronized or other suitable form or may be derivatized to produce a more soluble active product or to produce a pro-drug. The form of the resulting mixture depends upon a number of factors, including the intended mode of administration and the solubility of the components of the composition in the selected carrier or vehicle. The effective concentration is sufficient for ameliorating the symptoms of the condition and may be empirically determined.

C. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving the components of the composition provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the components of the composition. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected components of the composition. Such amount can be empirically determined.

D. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The components of the composition or pharmaceutically acceptable derivatives thereof may be formulated as aerosols for topical application, such as by inhalation. These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The components of the composition may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active components of the composition alone or in combination with other pharmaceutically acceptable excipients can also be administered.

These solutions, particularly those intended for ophthalmic use, may be formulated as 0.01% 10% (vol %) isotonic solutions, pH about 5.7, with appropriate salts.

E. Compositions for Other Routes of Administration

Other routes of administration, such as transdermal patches, including iontophoretic and electrophoretic devices, and rectal administration, are also contemplated herein.

Transdermal patches, including iontophoretic and electrophoretic devices, are well known to those of skill in the art.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

F. Targeted Formulations

The components of the composition provided herein, or pharmaceutically acceptable derivatives thereof, may also be formulated to be targeted to a particular tissue, receptor, or other area of the body of the subject to be treated. Many such targeting methods are well known to those of skill in the art. All such targeting methods are contemplated herein for use in the instant compositions.

In one embodiment, liposomal suspensions, including tissue-targeted liposomes, such as tumor-targeted liposomes, may also be suitable as pharmaceutically acceptable carriers. These may be prepared according to methods known to those skilled in the art. Briefly, liposomes such as multilamellar vesicles (MLV's) may be formed by drying down egg phosphatidyl choline and brain phosphatidyl serine (7:3 molar ratio) on the inside of a flask. A solution of the components of the composition provided herein in phosphate buffered saline lacking divalent cations (PBS) is added and the flask shaken until the lipid film is dispersed. The resulting vesicles are washed to remove unencapsulated components of the composition, pelleted by centrifugation, and then resuspended in PBS.

Kits of the Invention

According to another aspect of the invention, kits are provided, Kits according to the invention include package(s) comprising compositions of the invention.

The phrase "package" means any vessel containing compositions presented herein. In preferred embodiments, the package can be a box or wrapping. Packaging materials for use in packaging pharmaceutical products are well known to those of skill in the art. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

The kit can also contain items that are not contained within the package but are attached to the outside of the package, for example, pipettes.

Kits may optionally contain instructions for administering compositions of the present invention to a subject having a condition in need of treatment. Kits may also comprise instructions for approved uses of components of the composition herein by regulatory agencies, such as the United States Food and Drug Administration. Kits may optionally contain labeling or product inserts for the present compositions. The package(s) and/or any product insert(s) may themselves be approved by regulatory agencies. The kits can include compositions in the solid phase or in a liquid phase (such as buffers provided) in a package. The kits also can include buffers for preparing solutions for conducting the methods, and pipettes for transferring liquids from one container to another.

The kit may optionally also contain one or more other compositions for use in combination therapies as described herein. In certain embodiments, the package(s) is a container for intravenous administration. In other embodiments, compositions are provided in an inhaler. In still other embodiments compositions are provided in a polymeric matrix or in the form of a liposome.

The following examples are presented to illustrate the present invention and to assist one of ordinary skill in making and using the same. The examples are not intended in any way to otherwise limit the scope of the invention.

EXAMPLES

Example 1

Experimental Procedures

Experimental procedures used to demonstrate presence of BRAF oncogene mutation in rheumatoid arthritis patients and in particular rheumatoid arthritis synovial fibroblasts, transformation of rheumatoid arthritis synovial fibroblast by activating mutation of the BRAF oncogene, and reversal of BRAF-induced transformed rheumatoid arthritis synovial fibroblast phenotype by reducing total BRAF activity, indicating BRAF as target for therapeutic intervention in patients suffering from BRAF-induced rheumatoid arthritis.

RA Synovial Fibroblasts.

Synovial tissue was obtained with Institutional Review Board approval from 9 patients with severe RA patients and an 80 y/o woman with severe osteoarthritis (OA) undergoing joint replacement surgery. Patients with RA included 7 women and 2 men ages 30 to 74 years. Synovial tissues were digested with collagenase, and the resulting cells were filtered through sterile gauze, washed with Hanks BSS, reconstituted in 90% FCS and 10% DMSO, and stored frozen in liquid nitrogen until used. Synovial cells ($5\times10^6$–$20\times10^6$) were thawed at 37° C., immediately diluted 10-fold in DMEM/F12 (1:1) medium, centrifuged and reconstituted in DMEM/F12 medium containing 10% FCS and Hepes buffer. Synovial cells obtained from synovial tissues were added to T25 tissue flasks for 2 hours and then rinsed with Hanks BSS to remove non-adherent cells. Fresh DMEM/F12 (1:1) medium containing 5-10% FCS and Hepes buffer was added to the flasks and the cells were incubated at 37° C. in the presence of 5% $CO_2$ for 3 to 14 days. RNA was isolated from first passage synovial fibroblasts with the QIAamp RNA Blood Mini Kit (Qiagen, Sylmar, Calif.) according to the manufacturer's protocol.

PCR.

Reverse transcription PCR (RT-PCR) was performed with OneStep RT-PCR Kit™ (Qiagen, Valencia Calif.) according to the manufacturer's protocol. The forward primer was: 5'-GGGCCCCGGCTCTCGGTTAT-3' (SEQ ID NO:3), and the reverse primer was 5'-TGCTACTCTCCTGAA CTCTCT-CACTCA-3' (SEQ ID NO:4). These primers are located outside of the coding region of BRAF, BRAF sequences, both genomic and mRNA, can be obtained from publically accessible National Center for Biotechnology Information (NCBI; Bethesda, Md.) at the website: www.ncbi.nlm.nih.gov. The design of the primers used to analyze BRAF mRNA is based on the BRAF in RNA sequence obtained from NCBI under the NCBI Accession No. NM_004333.4. Nested PCR was done subsequently with primers inside of the coding region. The forward primer was 5'-GTTCAACGGGGACATGGA-3' (SEQ ID NO:5) beginning at nucleotide 54 from the ATG start site (exon 1) and the reverse primer was 5'-ATGGT-GCGTTTCCT GTCC-3' (SEQ ID NO:6) beginning at nucleotide 2279 of BRAF. Nested PCR was done with Easy A™ high fidelity cloning enzyme and mastermix (Agilent Technologies, Santa Clara, Calif.) with 1 microliter of the RT-PCR product as template. PCR conditions were 1 minute of denaturation at 94° C., 1 minute of annealing at 58° C., and 6 minutes of extension at 72° C. for 40 cycles. The PCR product was electrophoresed in 0.8% agarose, and cDNA was isolated from the gel with QIAquick Gel Extraction Kit (Qiagen, Valencia Calif.) according to the manufacturer's protocol. Purified DNA was sequenced by SeqWright, (Houston, Tex.) with the nested primers as well as internal primers. Nested PCR was also done with the "Fast COLD PCR" technique performed as described previously and analyzed by electrophoresis in 1.0% Seakem-1.0% Nusieve agarose gels (FMC BioProducts, Rockland Me.) (Li, J. and Makrigiorgos, G. M. (2009) *Biochem Soc Trans,* 37, 427-432). "COLD PCR" takes advantage of the lower melting temperatures of some mutant strands to facilitate their preferential amplification. Primers were designed to amplify a 191 bp fragment centered at V600. The unique restriction site SfcI was selected to identify mutations in the first nucleotide of V600R. The forward primer was 5'-ACTGCACAGGGCATG-GAT-3' (SEQ ID NO:7), and the reverse primer was 5'-TCTGG TGCCATCCACA AAA-3' (SEQ ID NO:8).

Restriction Enzyme Mapping.

BRAF contains a single SfcI restriction site that includes the first nucleotide of V600 codon. Complete digestion of BRAF with SfcI indicates the presence of wild-type sequence in both PCR amplified alleles. Mutations in nucleotides comprising the SfcI site are expected to result in partial, or incomplete cutting in the presence of excess enzyme. BRAF was digested with SfcI for 20 hours at 25° C. with a 10-fold excess of enzyme required for complete digestion.

siRNA Transfection.

RA fibroblasts were plated at 10-20% confluence overnight in 24-well plates and transfected in triplicate wells with Human BRAF On-Targetplus SMARTpool Cat# L-003460-00 and On-Target plus Control Pool Non-Targeting pool Cat# D-001810-10-05 (Thermo Scientific Dharmacon, Lafayette, Colo.) with Lipofectamine RNAiMAX (Invitrogen, Carlsbad, Calif.) according to the manufacturer's protocol for "forward transfection." Cells were counted in three separate areas of each well at the time siRNA was added and again 72 hour later. Data were expressed as mean number of cells in one microscopic field±SD of triplicate determinations. Significant inhibition of cell growth in response to BRAF siRNA compared to control siRNA was determined by Students t test. In order to confirm down-regulation of BRAF in response to BRAF siRNA, fibroblasts treated with BRAF siRNA and control siRNA were lysed in 10% SDS and evaluated for BRAF and actin by Western blotting to nitrocellulose after SDS-PAGE in 4-20% gradient gels (NuSep, Lawrenceville, Ga.). Nitrocellulose blots were incubated with rabbit antibodies to BRAF (Abgent, San Diego, Calif.) and goat antibodies to beta-actin (Santa Cruz Biotechnology, Santa Cruz, Calif.) followed by HRP-conjugated polyclonal goat anti-rabbit and rabbit anti-goat secondary antibodies, respectively. The blots were then developed with SuperSignal West Pico Chemiluminescent Substrate (Thermo Scientific, Rockford, Ill.) for detection of HRP and imaged with Chemi-Doc XRS (BioRad, Hercules, Calif.).

Results

Loss of Fibroblast Contact Inhibition.

Rheumatoid synovial fibroblasts showed absence of contact inhibition with a representative example shown (FIG. 1A). Loss of contact inhibition suggests that rheumatoid synovial fibroblasts have undergone transformation as previously described (Pap, T., et al. (2000) *Arthritis Res*, 2, 361-367; Karouzakis, E., et al. (2006) *Immunol Lett*, 106, 8-13; Mercer, K., et al. (2005) *Cancer Res*, 65, 11493-11500).

Characterization of BRAF Amplified from Synovial Fibroblasts by RT and Nested PCR.

Figure 2:
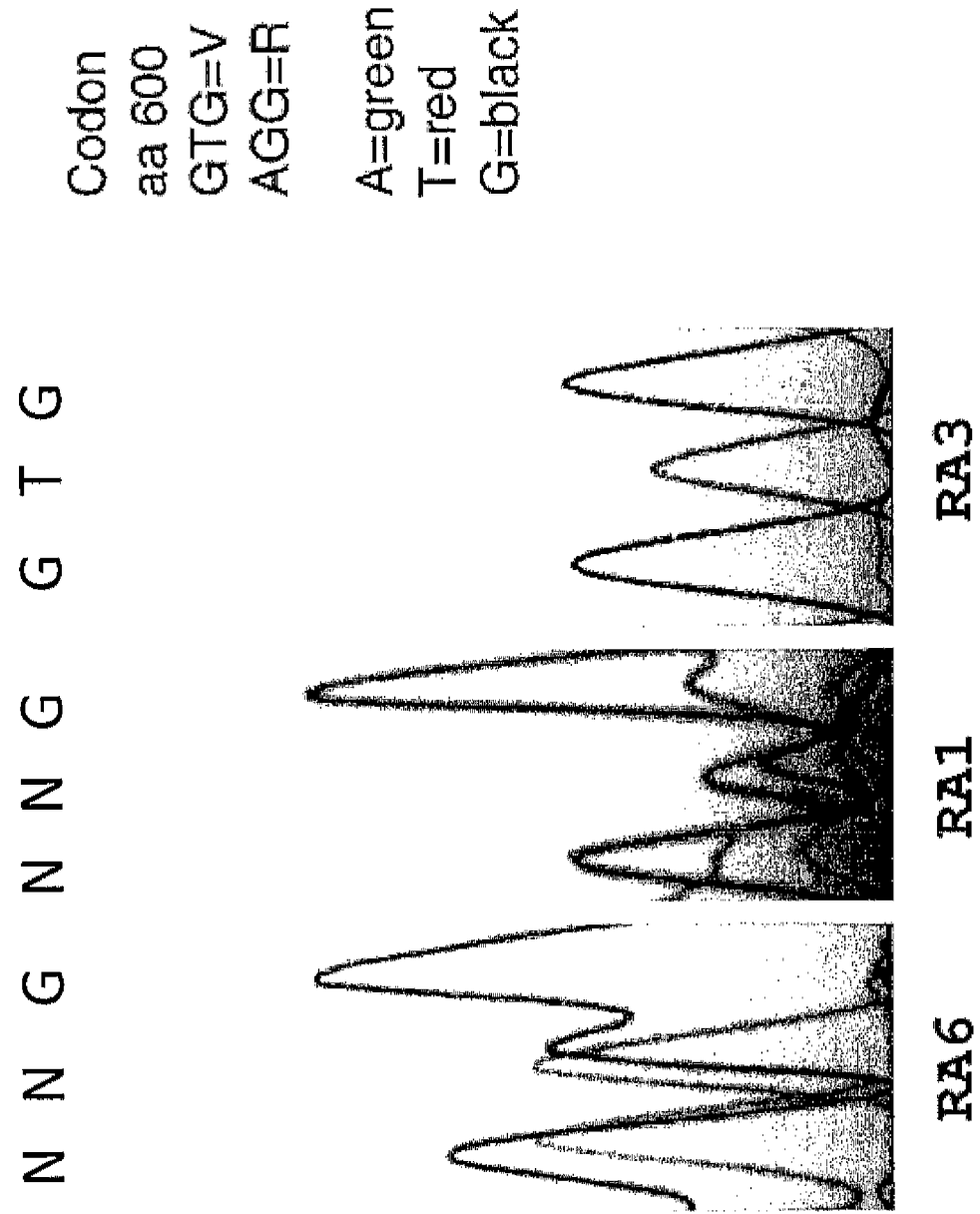
FIG. 2. Mutations of BRAF from rheumatoid synovial fibroblasts. V600R was identified in BRAF from RA synovial fibroblasts in 2 of 9 RA patients. The first two panels show chromatograms from RA1 and RA6 consistent with two separate nucleotide sequences encoding two different amino acids at residue 600, wild-type and V600R mutant. Panel 3 is a chromatogram from patient RA3 showing the wild-type nucleotide sequence encoding valine at residue 600.

RNA was isolated from first passage fibroblasts, reverse transcribed, and cDNA was amplified by PCR with primers outside of the coding region. Nested PCR with primers within the coding region resulted in a DNA fragment of the expected size with aberrant splice variants also evident in three patients (FIG. 1B). PCR products were subjected to electrophoresis in 0.8% agarose, and DNA was isolated from the gels. Direct DNA sequencing documented full-length BRAF from all patients as well as aberrant splice variants of BRAF in RA patients 6, 8, and 9 (FIG. 1B). DNA sequences of the splice variants showed the following exon deletions: RA6: exons 2-15, RAG: exons 3-8, RA9: exons 4-13 (FIG. 1C). RA8 splice variant retained the kinase domain but lacked exon 3 that contains a portion of the autoinhibitory domain that suppresses kinase activity (Tran, N. H., et al. (2005) *J Biol Chem*, 280, 16244-16253). BRAF splice variants that remove N-terminal autoinhibitory sequences have been associated with enhanced BRAF activity in cancer cells (Baitei, E. Y., et al. (2009) *J Pathol*, 217, 707-715; Tran, N. H., et al. (2005) *J Biol Chem*, 280, 16244-16253). Direct DNA sequencing of full-length transcripts with the antisense nested primer showed two separate sequences corresponding to residue 600 consistent with both wild-type and V600R mutation in synovial fibroblasts from patients 1 and 6 (FIG. 2). V600R is reported as a gain-of-function mutation with strong enhancement (250-fold) of BRAF activity (Wan, P. T., et al. (2004) *Cell*, 116, 855-867).

Restriction Enzyme Mapping.

Figure 3:
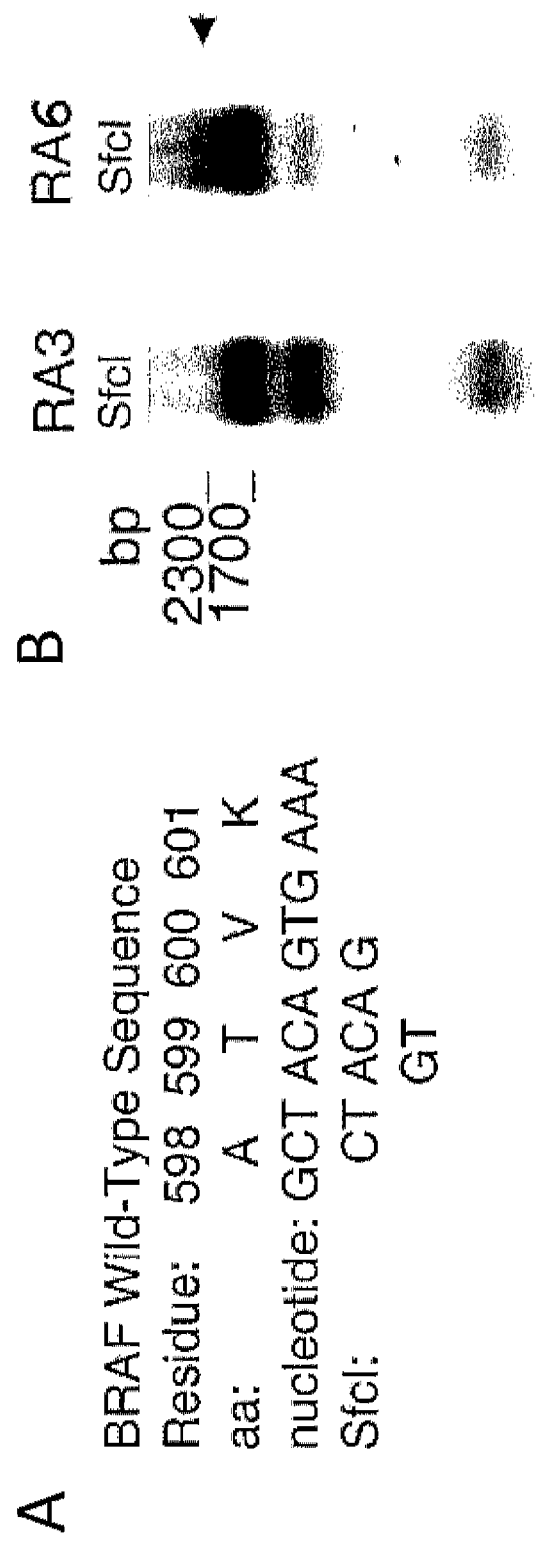
FIGS. 3A-3C. Restriction enzyme mapping.
Figure 3:
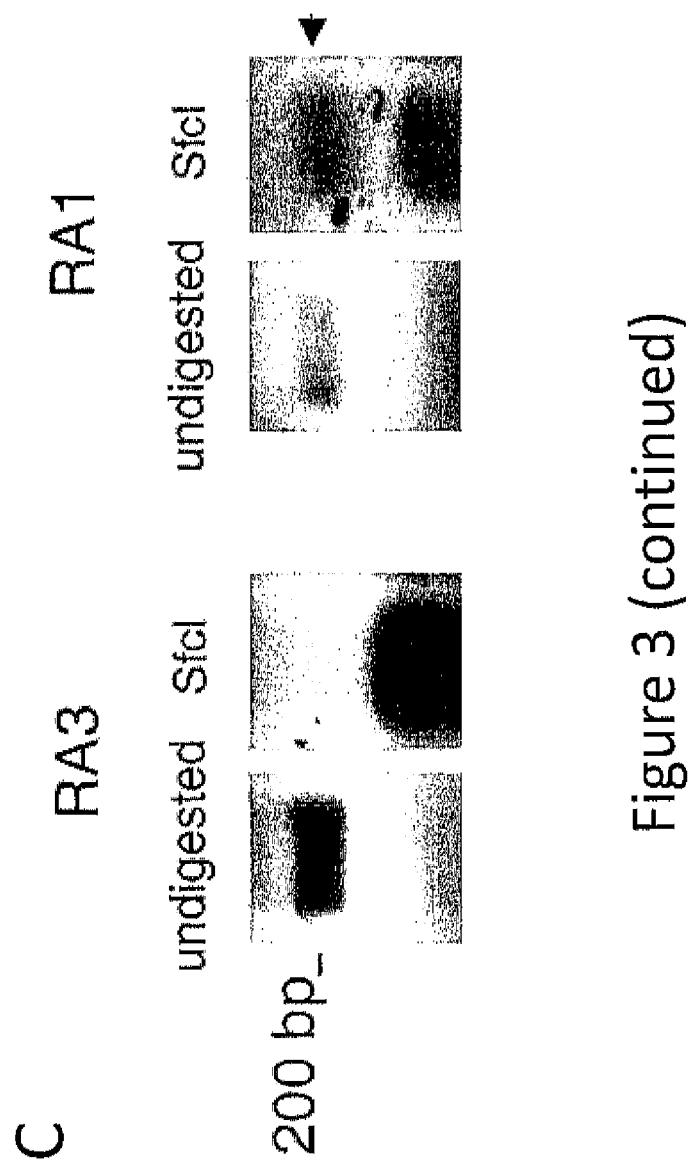

In order to confirm the mutations in BRAF cDNA, we performed restriction mapping of the region that includes V600. SfcI is a unique restriction site in BRAF that includes the first nucleotide of V600 codon (FIG. 3A). Incomplete digestion of 2300 bp BRAF cDNA to 1700 bp and 600 bp fragments in the presence of excess enzyme confirms the mutation V600R in cDNA. Therefore, cDNA from RA6 was digested with a 10-fold excess of SfcI and examined by gel electrophoresis. Incomplete digestion of the 2300 bp PCR product from RA6 was observed, consistent with the V600R mutation in RA6 cDNA (FIG. 3B). In contrast, SfcI completely digested the 2300 bp PCR product from RA3 without mutation of BRAF. In order to confirm the V600 mutation in RA1, we used "Fast COLD PCR" to enhance selection of mutant DNA strands as previously described (Li, J. and Makrigiorgos, G. M. (2009) *Biochem Soc Trans*, 37, 427-432). As shown, digestion of a 191 bp fragment, centered on V600, with an excess of SfcI failed to completely digest RA1 cDNA, consistent with the V600R mutation (FIG. 3C). In contrast, SfcI completely digested the 191 bp from RA3 without mutation of BRAF to produce two fragments, each approximately half the size of the 191 bp fragment.

BRAF Function in RA Synovial Fibroblasts.

Suppression of BRAF by siRNA inhibited growth of fibroblasts from both patients (RA1 & RA6) with V600R mutations of BRAF and from RA8 with the BRAF splice variant with an intact kinase domain but loss of a portion of the autoinhibitoxy domain. In contrast, BRAF-specific siRNA did not inhibit growth of synovial fibroblasts from RA2 and RA4 without mutations of BRAF. In addition, BRAF siRNA did not inhibit growth of fibroblasts from patient OA7 with osteoarthritis (FIG. 4A). BRAF siRNA inhibited the production of BRAF as demonstrated by Western blotting of synovial fibroblast lysates from patient RA6 (FIG. 4B).

Discussion

The RAS/RAF/MEK/ERK pathway is referred to as the mitogen-activated protein kinase (MAPK) pathway. Activation of MAPK results in cell proliferation, survival, and transformation. BRAF is one of three isoforms of RAF, but only BRAF is frequently mutated in various cancers (Garnett, M. J. and Marais, R. (2004) *Cancer Cell*, 6, 313-319). Some mutations in the activation segment of BRAF kinase have gain-of-function activity responsible for cellular transformation leading to melanoma and other cancers (Wan, P. T., et al. (2004) *Cell*, 116, 855-867). The observation that mutations of BRAF induce transformation of embryonic fibroblasts, but not several other somatic cells, led us to search for similar mutations in RA synovial fibroblasts as a mechanism for their transformation (Mercer, K., et al. (2005) *Cancer Res*, 65, 11493-11500). Residue 600 is most frequently mutated with V600E predominating. V600R occurs less frequently but is also a strong (250-fold) enhancer of BRAF kinase activity (Wan, P. T., et al. (2004) *Cell*, 116, 855-867). Identification of V600R gain-of-function mutations of BRAF in RA synovial fibroblasts in RA patients is consistent with this as a potential mechanism for synovial fibroblast transformation in the pathogenesis of erosive joint disease in some patients. BRAF siRNA inhibited growth of synovial fibroblasts from both patients with BRAF V600R mutations, confirming the functional significance of BRAF mutations on synovial fibroblast growth.

BRAF has two normal isoforms associated with multiple splice variants. However, aberrant splice variants of BRAF were recently reported in both colon and thyroid cancers (Baitei, E. Y., et al. (2009) *J Pathol,* 217, 707-715; Seth, R., et al. (2009) *Gut,* 58, 1234-1241). Some aberrant splice variants have been shown to activate the MAP kinase signaling pathway suggesting that BRAF splice variants may function as an alternative mechanism for oncogenic BRAF activation (Seth, R., et al. (2009) *Gut,* 58, 1234-1241). Consistent with this idea, a BRAF N-terminal autoinhibitory domain has been identified, and loss of the inhibitory domain resulted in increased BRAF kinase activity (Lefevre, S., et al. (2009) *Nat Med,* 15, 1414-1420). Thus, certain aberrant isoforms that exclude portions of the autoinhibitory domain but retain the kinase domain may have enhanced kinase activity. In our study, one RA patient (RA8) had an aberrant BRAF splice variant with deletion of exon 3 containing a portion of the autoinhibitory domain; however, an intact kinase domain was retained. Proliferation of synovial fibroblasts from RA8 was inhibited by BRAF-specific siRNA. The finding of gain-of-function BRAF mutations and splice variants is consistent with multiple mechanisms involving BRAF that may lead to transformation of fibroblasts in RA synovium.

Patients with cancers due to mutations of oncogenes often produce antibodies to altered or cryptic epitopes. Mutations of BRAF occur in 15% of cancers with the highest incidence in melanomas where 9% of patients have serum antibodies specific for BRAF (Davies, H., et al. (2002) *Nature,* 417, 949-954; Fensterle, J., et al. (2004) *BMC Cancer,* 4, 62). In a recent study, 9 of 19 patients with rheumatoid arthritis were reported to have serum antibodies to BRAF assayed by Western blot, a finding that is consistent with the presence of an altered BRAF protein in these patients (Auger, I., et al. (2009) *Ann Rheum Dis,* 68, 591-594). We did not have matched serum samples to evaluate a correlation between the presence of serum antibodies to BRAF and BRAF mutations or aberrant splice variants in synovial fibroblasts. Further studies are required to evaluate these associations. It is likely that our study underestimates the frequency of BRAF mutations in RA synovial fibroblasts due to the technical difficulty inherent in identifying heterozygous mutations. In addition, some aberrant splice variants lacking the autoinhibitory domain would be missed as a result of our selection of PCR primers requiring the presence of exon 1.

Synovial fibroblasts destroy articular cartilage and bone in rheumatoid arthritis. It is the discovery of the invention that mutations of the BRAF gene can transform synovial fibroblasts responsible for the destruction of articular cartilage and bone in rheumatoid arthritis and identifies BRAF gene as a new target for therapeutic intervention.

Transformation of synovial fibroblasts in RA patients by mutant BRAF protein due to mutations in the BRAF gene include or may include, but are not limited to, loss of synovial fibroblast contact inhibition of cellular growth, increase in cellular proliferation, ability to grow in soft agar, increase in cellular mobility, ability to migrate and accumulate at cartilage and/or bone, ability to migrate and accumulate at cartilage and/or bone using in vivo model systems, anchorage-independent growth, morphological changes, focus formation on a monolayer, increase in life span or immortalization, and/or tumorigenicity in nude mice.

Role for mutant BRAF protein in the transformation of synovial fibroblast responsible for destruction of articular cartilage and bone in rheumatoid arthritis is defined by the presence of activating BRAF gene mutations in rheumatoid synovial fibroblasts. Characterization of the BRAF gene from rheumatoid synovial fibroblasts from 9 rheumatoid arthritis patients showed mutation of codon 600 of exon 15 changing valine 600 encoded by GTG to arginine encoded by AGG for RA6 patient and AGA for RA1 patient (FIG. 2). In one publication, valine 600 of BRAF was previously designated valine 599 in the 5' coding region of BRAF (Wellbrock, C., et al. (2004) *Nat Rev Mol Cell Biol,* 5, 875-885). Presence of this V600R gain-of-function point mutation in BRAF protein significantly activates basal BRAF kinase activity (Wan, P. T., et al. (2004) *Cell,* 116, 855-867). With increasing sample size beyond 9 rheumatoid arthritis patients so far analyzed by us, it is anticipated that other codons, CGT, CGC, CGA, and CGG, for arginine may also encode for BRAF V600R mutation.

In addition to V600R gain-of-function BRAF mutation, other BRAF mutations are anticipated to transform synovial fibroblasts responsible for the destruction of articular cartilage and bone in rheumatoid arthritis. Point mutations affecting kinase activity and cellular transformation have been described for BRAF from a number of human cancers. These gain-of-function point mutations occur primarily in the kinase domain concentrating in and/or around the activation segment, a region of 10-30 amino acids bounded by almost invariant DFG and APE motifs, and in the glycine-rich P loop of the N lobe (Wan, P. T., et al. (2004) *Cell,* 116, 855-867; Davies, H., et al. (2002) *Nature,* 417, 949-954). The P loop interacts with the activation segment to keep BRAF in an inactive conformation (see FIG. 4 of Wan, P. T., et al. (2004) *Cell,* 116, 855-867). Similar to activated RAS phosphorylation of BRAF threonine 599 (major activation segment phosphorylation site) and serine 602 (minor activation segment phosphorylation site), the mis-sense mutations in P loop or activation segment can activate BRAF by destabilizing inactive and/or stabilizing active kinase conformation (Wan, P. T., et al. (2004) *Cell,* 116, 855-867).

The region around BRAF activation segment extends from amino acid 583 to 623 of SEQ ID NO:2 with the BRAF activation sequence from amino acid 594-623, as is given below, with highly conserved residues found to be mutated in a number of human cancers indicated by bold and double underline (Wan, P. T., et al. (2004) *Cell,* 116, 855-867; Davies, H., et al. (2002) *Nature,* 417, 949-954; Garnett, M. J. and Marais, R. (2004) *Cancer Cell,* 6, 313-319):

594 FLHEDLTVKIGDFGLATVKSRWSGSHQFEQLSGSILWMAPE 623

Anticipated BRAF mis-sense mutations in or around BRAF activation segment are expected to transform synovial fibroblasts responsible for the destruction of articular cartilage and bone in rheumatoid arthritis are: E586K, D587A, D594D, D594K, D594V, F595L, G596R, L597Q, L597R, L597S, L597V, T599I, V600D, V600E, V600G, V600K, K600M, K601E, and K601N. These mutations are based on documented BRAF mis-sense mutations in human cancers (Wan, P. T., et al. (2004) *Cell,* 116, 855-867; Davies, H., et al. (2002) *Nature,* 417, 949-954; Garnett, M. J. and Marais, R. (2004) *Cancer Cell,* 6, 313-319).

Figure 4:
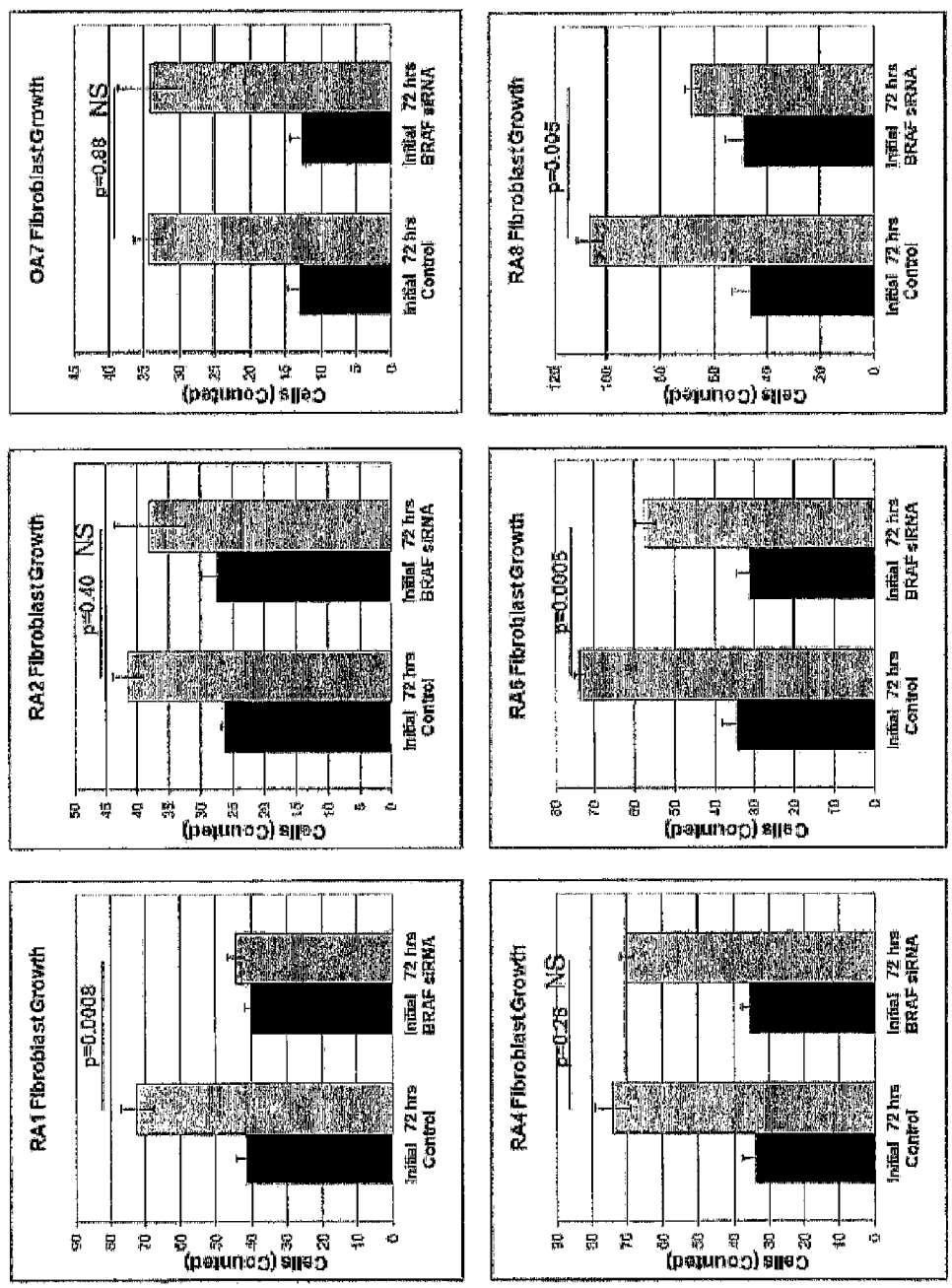
FIGS. 4A-4B. Inhibition of RA fibroblast growth by BRAF siRNA.
Figure 5:
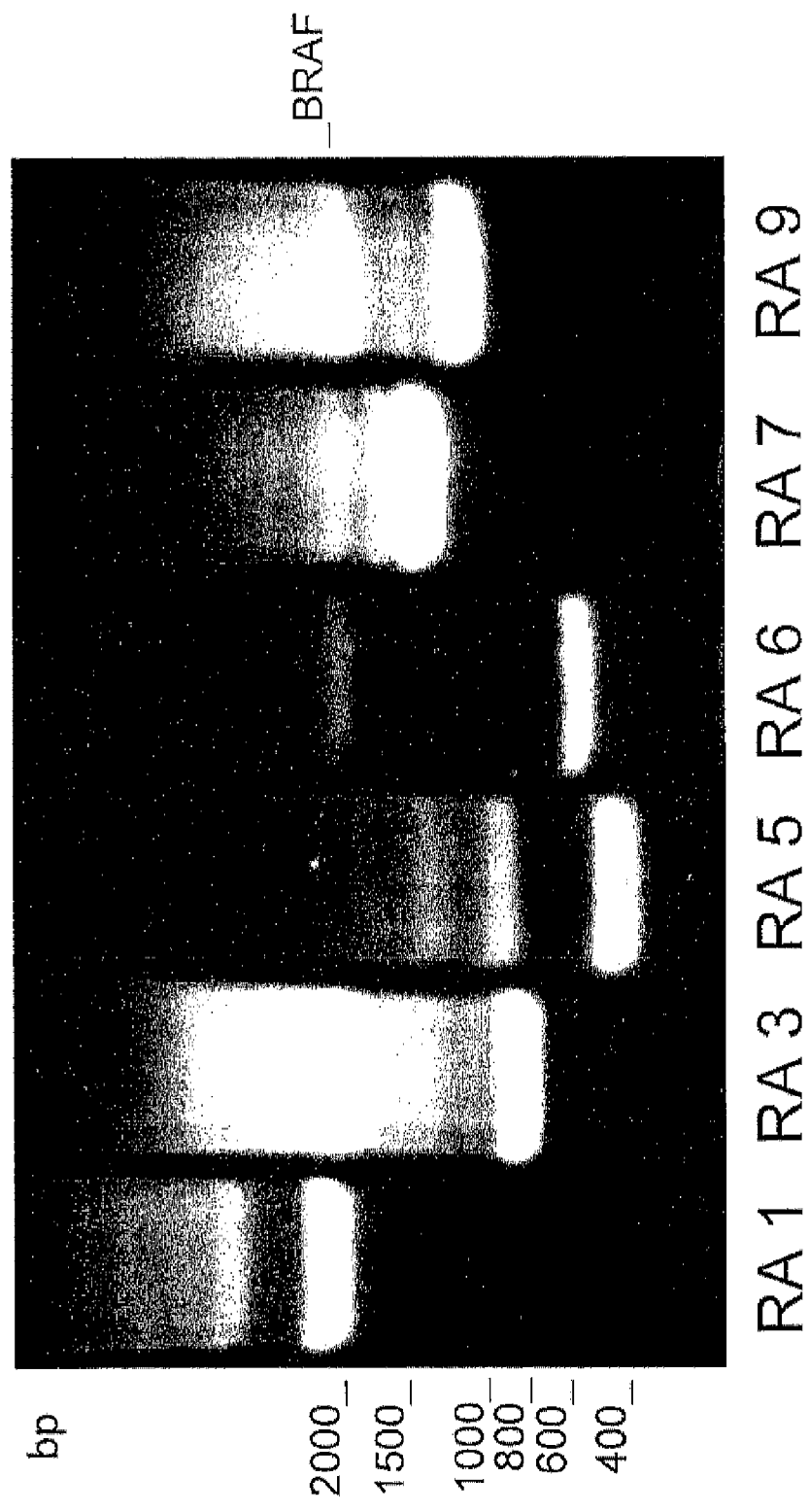
FIGS. 5A-5B. BRAF Aberrant Splice Variants in Rheumatoid Arthritis Synovial Fibroblasts.
Figure 5:
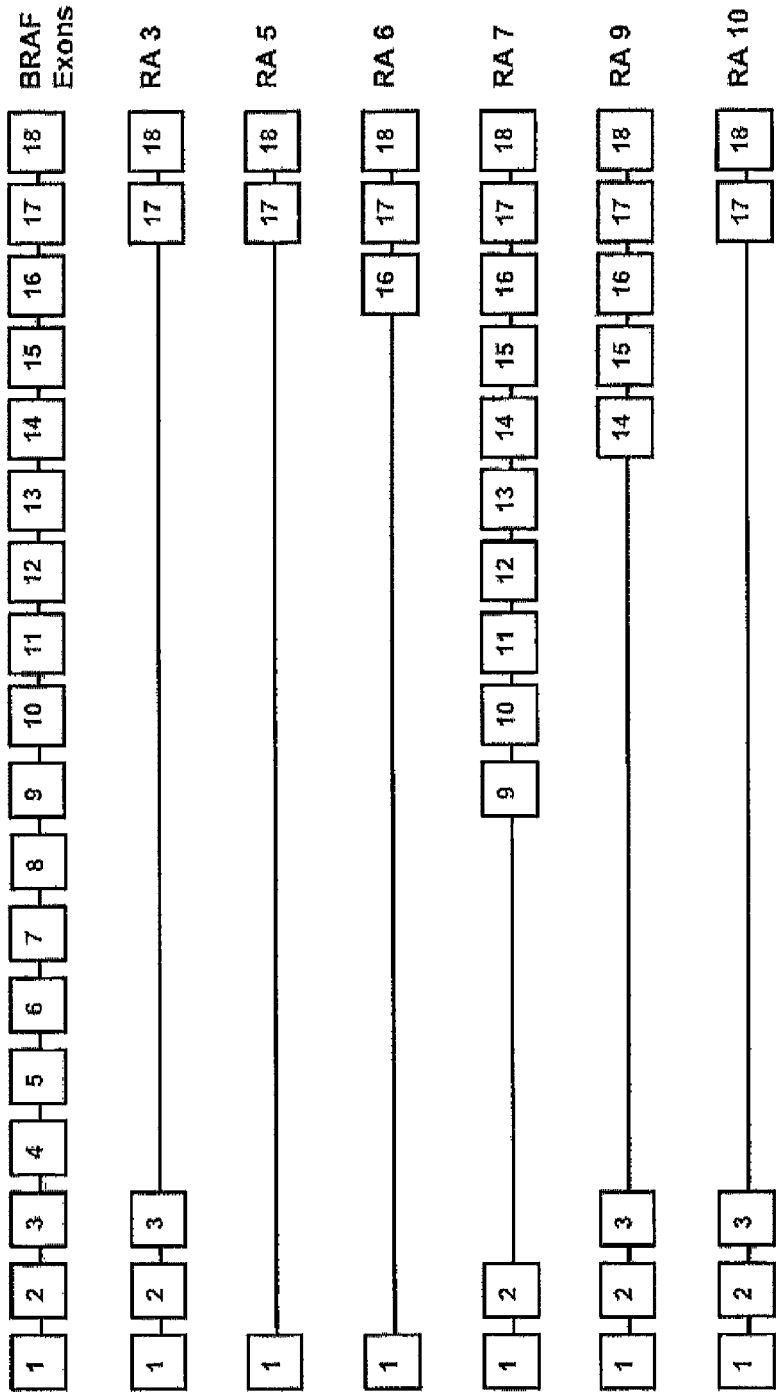
Figure 7:
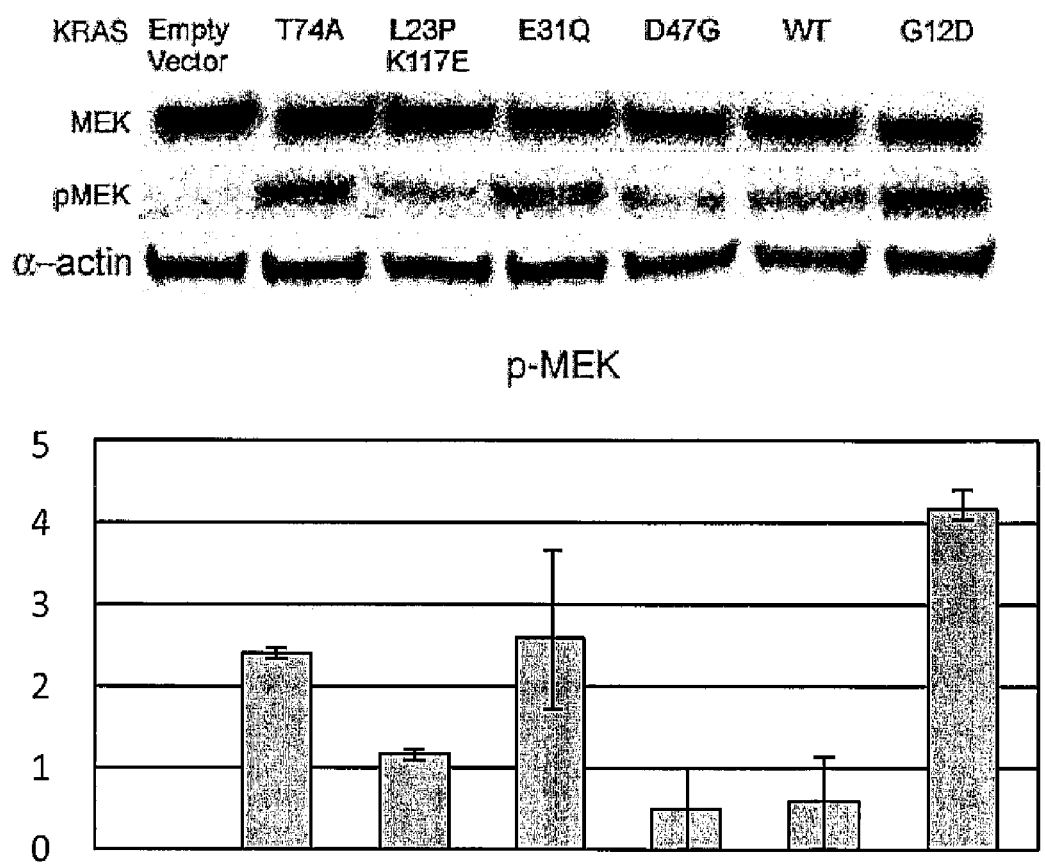
FIG. 7. COS-7 cells transfected with an expression vector containing KRAS mutants in order to determine whether KRAS mutations were responsible for constitutive MAPK activation. Mutant G12D served as a positive control. Mutants T74A and E31Q constitutively activated MAPK activity.

The P loop is part of the N lobe in the crystal structure of BRAF (see FIG. 4 of Wan, P. T., et al. (2004) *Cell,* 116, 855-867) and extends from amino acid 462-469 of SEQ ID NO:2 containing a highly conserved glycine-rich motif, GXGXXG motif (see FIG. 2b of Davies, H., et al. (2002) *Nature,* 417, 949-954), with the sequence given below and residues found to be mutated in a number of human cancers indicated by bold and double underline:

462        RIGSGSFG        469

The BRAF mis-sense mutations in P loop that are expected to transform synovial fibroblasts responsible for the destruction of articular cartilage and bone in rheumatoid arthritis are: R462I, I463S, G464E, G464R, G464V, G466A, G466E, G466R, G466V, F468C, G469A, G469E, G469R, G469S, and G469V.

Additional mutations outside of the activation segment region and P loop but within the kinase domain found in human cancers are: V459L, K475E, N581S, R682Q, and A728V (Wan, P. T., et al. (2004) *Cell,* 116, 855-867; Davies, H., et al. (2002) *Nature,* 417, 949-954; Garnett, M. J. and Marais, R. (2004) *Cancer Cell,* 6, 313-319). Other BRAF mis-sense mutations are: M117R, 1326T, K439Q, K439T, T440P, and V459L (Wan, P. T., et al. (2004) *Cell,* 116, 855-867; Davies, H., et al. (2002) *Nature,* 417, 949-954; Garnett, M. J. and Marais, R. (2004) *Cancer Cell,* 6, 313-319). Furthermore, a more extensive listing of BRAF mutations in human cancers can be found at the website (http://www.sanger.ac.uk/genetics/CGP/cosmic) using the search term BRAF. While this listing is not meant to be exhaustive, these BRAF mis-sense mutations within the context of synovial fibroblasts are anticipated to transform the fibroblasts responsible for the destruction of articular cartilage and bone in rheumatoid arthritis.

It is noted that V600E mis-sense mutation may account for at least 80% of BRAF mutations in human cancers (Wan, P. T., et al. (2004) *Cell,* 116, 855-867; Davies, H., et al. (2002) *Nature,* 417, 949-954; Garnett, M. J. and Marais, R. (2004) *Cancer Cell,* 6, 313-319).

In addition to the mis-sense, gain-of-function mutations, the RAS-RAF-MEK-ERK signal transduction pathway can become altered by the presence of internally truncated BRAF proteins, resulting in transformation of rheumatoid synovial fibroblasts. Aberrantly spliced BRAF transcripts were found in some rheumatoid synovial fibroblasts, resulting in loss of BRAF coding sequences corresponding to exons 2-15, exons 2-16, exons 3-8, exons 4-13, and exons 4-16. In the case of exon 3-8 deletion, in which the auto-inhibitory domain of BRAF is deleted while the kinase domain remains intact, the internally truncated BRAF protein promoted cellular growth of the affected rheumatoid synovial fibroblasts. The constitutively active BRAF kinase phosphorylates and activates MEK1/2 proteins, ultimately resulting in increased proliferation of synovial fibroblast cells. Analysis of rheumatoid synovial fibroblasts from additional rheumatoid arthritis patients will provide more examples of other aberrantly spliced BRAF transcripts differing in the exons deleted from the mRNA transcript.

Finding aberrantly spliced transcripts for BRAF in rheumatoid synovial fibroblasts is significant and these, like the mis-sense BRAF mutant transcripts, are also therapeutic targets in the treatment of rheumatoid arthritis. Internally truncated BRAF proteins, e.g. in which exons 4-15 or 2-17 are deleted, are reported to promote cellular transformation, mediated perhaps through activation of the RAS-RAF-MEK-ERK/MAP kinase signaling pathway leading to increased phosphorylation and activation of ERK kinase protein (Baitei, E. Y., et al. (2009) *J Pathol,* 217, 707-715). In the case of exon 2-17 deletion, it is noteworthy that both the auto-inhibitory domain and almost the entire kinase domain are missing in the truncated protein. Yet, this truncated protein, obtained from translation of exon 1 and 18, can promote cellular transformation. It is anticipated that truncated, internally deleted BRAF proteins from aberrantly spliced BRAF transcripts will similarly transform synovial fibroblast. It is significant that a number of aberrantly spliced BRAF transcripts were present in rheumatoid synovial fibroblast, and these aberrant transcripts and associated proteins serve as therapeutic targets in rheumatoid arthritis.

In addition to mis-sense mutation and aberrant RNA splicing, mutant BRAF gene and protein with internal deletion(s) and/or insertion(s) are anticipated. Such changes in rheumatoid synovial fibroblast can lead to transformation of synovial fibroblast, and as such, these BRAF genes and proteins are therapeutic target in rheumatoid arthritis.

It is noted that in addition to the BRAF coding sequence and protein sequence shown in SEQ ID NO:1, additional isoforms of BRAF exist. For example, an isoform of BRAF is due to alternative splicing of exon 8b between exons 8 and 9 (encoding "EKFPEVELQDNR" which when present is inserted, e.g., between aspartic acid 380 and aspartic acid 381 of SEQ ID NO:2) and/or alternative splicing of exon 9b between exons and 10 of SEQ ID NO:1 (encoding "APLN-QLMRCLRKYQSRTPSPLLHSVPSEIVFDFEPGPVFR" which when present is inserted between glycine 392 and glycine 393 of SEQ ID NO:2) (Hmitou, I., et al. (2007) *Mol Cell Biol,* 27, 31-43). The four different BRAF isoforms are differentially regulated which in turn affects downstream MEK activation (Hmitou, I., et al, (2007) *Mol Cell Biol,* 27, 31-43). It is expected that these BRAF isoforms will be present in rheumatoid synovial fibroblasts. In addition, BRAF mutations, described above, may be present in BRAF isoforms, and as such, these BRAF isoforms and their mutants are potential therapeutic targets in rheumatoid arthritis.

Discovery that BRAF mutations are found in rheumatoid synovial fibroblast from rheumatoid arthritis patients provides a therapeutic target in the treatment of rheumatoid arthritis. Presence of BRAF mutations transform rheumatoid synovial fibroblast, and to assess the involvement of BRAF in transformation of rheumatoid synovial fibroblast, a method is described in which the activated BRAF mutant protein expression is decreased through the use of e.g. siRNA (small interfering RNA) directed against BRAF sequences and the treated cells assessed for transformed phenotype, such as contact inhibition and/or cellular proliferation. Unlike wild-type BRAF protein, loss of mutant BRAF protein expression reverses the transformed synovial fibroblast phenotype, indicating that a subject is suffering from a rheumatoid arthritis associated with the BRAF oncogene. Protocols for the isolation of synovial fibroblasts, cell culture condition of the isolated primary synovial fibroblast, treatment with siRNA, and assays for contact inhibition and cell proliferation are provided.

Double stranded RNA(s) can suppress expression of a specific gene of interest in a homology-dependent manner in a process called "RNA interference" or "RNAi" by targeting mRNA molecules for degradation (Sharp, P. A. and Zamore, P. D. (2000) *Science,* 287, 2431-2433; Bosher, J. M. and Labouesse, M. (2000) *Nat Cell Biol,* 2, E31-36). SiRNAs are small interfering RNAs which are double-stranded RNA molecules with approximately 20-25 nucleotides in length that participate in the RNAi pathway. Typically, siRNAs have a short double-stranded RNA region (usually 21 bp) with a 2-nucleotide overhang. A number of commercial companies (such as Thermo Fisher Dharmacon and OriGene) supply either unmodified or modified siRNAs designed to knockdown BRAF transcript levels and consequently BRAF protein expression.

To obtain long term down-regulation of BRAF expression, siRNA expression vector may be introduced into synovial fibroblast cells with a loop between two strands homologous to BRAF sequences to produce short hairpin RNA (shRNA) produced by RNA polymerase III transcription using RNA polymerase III promoter, such as U6 or H1. In addition, promoters for shRNA genes, such as U1, may be used to produce shRNAs. The shRNAs are processed to produce siRNAs for down-regulation of BRAF transcript level and consequently BRAF protein level. Design and production of siRNAs and shRNAs toward BRAF are discussed in U.S. patent application Ser. No. 10/834,665 entitled "Treatment of Cancer by Inhibiting BRAF Expression," filed on Jun. 3, 2003 and U.S. patent application Ser. No. 11/270,796 entitled "Treatment of Cancer by Simultaneous Inhibition of BRAF and Restoration or Mimicry of p16$^{INK4A}$ Activity," filed on Nov. 8, 2005 and BRAF shRNA expression constructs may be obtained from commercial sources, such as GeneCopoeia, OriGene, and Qiagen SABiosciences.

In addition to siRNAs and shRNAs, BRAF expression may be down-regulated by the use of precursor microRNAs (miRNAs) expression vector used to produce precursor miRNAs and subsequent processing to miRNAs. Mature miRNAs usually directed to the 3' untranslated region (3' UTR) down-regulates gene expression either by mRNA degradation or interfering with translation (Bartel, D. P. (2009) Cell, 136, 215-233). The miRNAs for BRAF may be obtained from commercial sources, such as GeneCopoeia and OriGene. Thus, siRNA, shRNA, and/or miRNA to BRAF can be used to down-regulated BRAF expression and determine if BRAF gene is associated with transformation of rheumatoid synovial fibroblasts in rheumatoid arthritis, thereby establishing whether a subject is suffering from a rheumatoid arthritis associated with the BRAF oncogene.

Other methods based on homology to the BRAF nucleic acid sequence could be used to downregulate BRAF expression and these would also include use of anti-sense nucleic acid approaches, including but not limited to short anti-sense oligonucleotides (DNA or RNA) or long anti-sense RNA transcripts, ribozymes, etc. It should also be noted that the introduced nucleic acid to downregulate BRAF expression by targeting BRAF nucleic acid sequences may be unmodified RNA or alternatively chemically modified (e.g., incorporation of 2'-O-methyl or 2'-O-methoxyethyl-group) so as to increase efficiency of delivery, reduce non-specific degradation by nucleases, increase efficiency of targeting BRAF sequences, reduce off-target effects, etc.

BRAF inhibitors may be used to assess if a subject is suffering from a rheumatoid arthritis associated with the BRAF oncogene. Use of BRAF inhibitors in the absence of activated RAS is expected to inhibit cell proliferation and promote cell death (19). However, its use in activated RAS cells results in MEK-ERK activation by promoting dimerization of CRAF, one of three RAF isoforms, with wild-type. BRAF or kinase-dead BRAF, or another CRAF monomer which are kinase-active dimers (Cichowski, K. and Janne, P. A. (2010) Nature, 464, 358-359). Thus, by knowing the status of RAS, it is anticipated that BRAF inhibitors may be used in the absence of RAS mutation to determine if a subject is suffering from a rheumatoid arthritis associated with the BRAF oncogene.

Using art known to a skilled professional, mutation in the BRAF sequence can be determined by extracting RNA from synovial fibroblast, RT-PCR, and nested PCR with BRAF primers to obtain BRAF cDNA which can be further subjected to sequence determination and/or to restriction enzyme digestion analysis with SfcI restriction enzyme. BRAF V600R mutation can be identified on the basis of sequence and its presence is consistent with loss of SfcI cleavage at codon 600. While electrophoretic analysis of PCR products can show presence of aberrantly spliced transcripts, sequence determination can be used to definitely demonstrate the nature of the aberrantly spliced transcripts. Mutations in the BRAF nucleic acid may also be directly determined by analyzing BRAF genomic DNA with PCR, DNA sequence determination, and restriction enzyme analysis. Standard molecular biology techniques may be found in Ausubel, F. M. (2002) *Short protocols in molecular biology: a compendium of methods from Current protocols in molecular biology.* 5th ed. Wiley, New York; Ausubel, F. M. (1987) *Current protocols in molecular biology*. Published by Greene Pub. Associates and Wiley-Interscience: J. Wiley, New York; and Sambrook, J. and Russell, D. W. (2001) *Molecular cloning: a laboratory manual*. 3rd ed. Cold Spring Harbor Laboratory Press, Cold Spring Harbor, N.Y.

Finally, by establishing BRAF as a therapeutic target in the treatment of rheumatoid arthritis, the current invention provides a rationale for treatment of rheumatoid arthritis patients. BRAF or RAF inhibitors, which may work by binding directly to BRAF, may be used to reverse synovial fibroblast transformation dependent on BRAF mutant protein or truncated BRAF protein. Use of specific inhibitors to treat rheumatoid arthritis should also take RAS status into account. Examples of BRAF or RAF inhibitors include but are not limited to: PLX4032 (Plexxikon, Inc., Berkeley, Calif.; (Tap, W. D., et al. (2010) Neoplasia, 12, 637-649)), RAF265 (CHIR-26; Novartis Pharmaceuticals, Basel, Switzerland), Sorafenib (BAY43-9006; Bayer, Pittsburgh, Pa.), XL281 (Exelixis, San Francisco, Calif.), 513-590885 (SmithKline Beecham, Philadelphia, Pa.), and PLX4720 (Plexxikon, Inc., Berkeley, Calif.). In addition, since MEK and ERK are downstream targets of RAF, compounds that directly bind to MEK or ERK kinases may serve as MEK or ERK inhibitors, respectively (Wong, K. K. (2009) *Recent Pat Anticancer Drug Discov*, 4, 28-35), and such compounds may also be beneficial in treating rheumatoid arthritis patients. Such MEK inhibitors include AZD6244 (ARRY-142886; AstraZeneca, London, England), PD0325901, CI-1040, and XL518 (Exelixis, San Francisco, Calif.). In addition, ERK inhibitors include FR180204 (EMD4Biosciences, Merck KGaA, Darmstadt, Germany), CAY10561 and 328006 (Merck KGaA, Darmstadt, Germany). The list above is by no means exhaustive and the compounds listed above are for illustrative purposes only.

REFERENCES

1. Muller-Ladner, U., Kriegsmann, J., Franklin, B. N., Matsumoto, S., Geiler, T., Gay, R. E. and Gay, S. (1996) Synovial fibroblasts of patients with rheumatoid arthritis attach to and invade normal human cartilage when engrafted into SCID mice. *Am J Pathol*, 149, 1607-1615.
2. Pap, T., Muller-Ladner, U., Gay, R. E. and Gay, S. (2000) Fibroblast biology. Role of synovial fibroblasts in the pathogenesis of rheumatoid arthritis. *Arthritis Res*, 2, 361-367.
3. Buckley, C. D., Pilling, D., Lord, J. M., Akbar, A. N., Scheel-Toellner, D. and Salmon, M. (2001) Fibroblasts regulate the switch from acute resolving to chronic persistent inflammation. *Trends Immunol*, 22, 199-204.
4. Muller-Ladner, U., Pap, T., Gay, R. E., Neidhart, M. and Gay, S. (2005) Mechanisms of disease: the molecular and cellular basis of joint destruction in rheumatoid arthritis. *Nat Clin Pract Rheumatol*, 1, 102-110.
5. Pap, T., Meinecke, I., Muller-Ladner, U. and Gay, S. (2005) Are fibroblasts involved in joint destruction? *Ann Rheum Dis*, 64 Suppl 4, iv52-54.
6. Karouzakis, E., Neidhart, M., Gay, R. E. and Gay, S. (2006) Molecular and cellular basis of rheumatoid joint destruction. *Immunol Lett*, 106, 8-13.
7. Huber, L. C., Distler, O., Tarner, I., Gay, R. E., Gay, S. and Pap, T. (2006) Synovial fibroblasts: key players in rheumatoid arthritis. *Rheumatology (Oxford)*, 45, 669-675.
8. Mercer, K., Giblett, S., Green, S., Lloyd, D., DaRocha Dias, S., Plumb, M., Marais, R. and Pritchard, C. (2005) Expression of endogenous oncogenic V600EB-raf induces proliferation and developmental defects in mice and transformation of primary fibroblasts. *Cancer Res*, 65, 11493-11500.
9. Lefevre, S., Knedla, A., Tennie, C., Kampmann, A., Wunrau, C., Dinser, R., Korb, A., Schmaker, E. M., Tarner, I. H., Robbins, P. D. et al. (2009) Synovial fibroblasts spread rheumatoid arthritis to unaffected joints. *Nat Med*, 15, 1414-1420.
10. Wellbrock, C., Karasarides, M. and Marais, R, (2004) The RAF proteins take centre stage. *Nat Rev Mol Cell Biol*, 5, 875-885.
11. Wan, P. T., Garnett, M. J., Roe, S. M., Lee, S., Niculescu-Duvaz, D., Good, V. M., Jones, C. M., Marshall, C. J., Springer, C. J., Barford, D. et al. (2004) Mechanism of activation of the RAF-ERK signaling pathway by oncogenic mutations of B-RAF. *Cell*, 116, 855-867.
12. Davies, H., Bignell, G. R., Cox, C., Stephens, P., Edkins, S., Clegg, S., Teague, J., Woffendin, H., Garnett, M. J., Bottomley, W. et al. (2002) Mutations of the BRAF gene in human cancer. *Nature*, 417, 949-954.
13. Garnett, M. J. and Marais, R. (2004) Guilty as charged: B-RAF is a human oncogene. *Cancer Cell*, 6, 313-319.
14. Baitei, E. Y., Zou, M., Al-Mohanna, F., Collison, K., Alzahrani, A. S., Farid, N. R., Meyer, B. and Shi, Y. (2009) Aberrant BRAF splicing as an alternative mechanism for oncogenic B-Raf activation in thyroid carcinoma. *J Pathol*, 217, 707-715.
15. Hmitou, I., Druillennec, S., Valluet, A., Peyssonnaux, C. and Eychene, A. (2007) Differential regulation of B-raf isoforms by phosphorylation and autoinhibitory mechanisms. *Mol Cell Biol*, 27, 31-43.
16. Sharp, P. A. and Zamore, P. D. (2000) Molecular biology. RNA interference. *Science*, 287, 2431-2433.
17. Bosher, J. M. and Labouesse, M. (2000) RNA interference: genetic wand and genetic watchdog. *Nat Cell Biol*, 2, E31-36.
18. Bartel, D. P. (2009) MicroRNAs: target recognition and regulatory functions. *Cell*, 136, 215-233.
19. Cichowski, K. and Janne, P. A. (2010) Drug discovery: inhibitors that activate. *Nature*, 464, 358-359.
20. Ausubel, F. M. (2002) *Short protocols in molecular biology: a compendium of methods from Current protocols in molecular biology*. 5th ed. Wiley, New York.
21. Ausubel, F. M. (1987) *Current protocols in molecular biology*. Published by Greene Pub. Associates and Wiley-Interscience: J. Wiley, New York.
22. Sambrook, J. and Russell, D. W. (2001) *Molecular cloning: a laboratory manual*. 3rd ed. Cold Spring Harbor Laboratory Press, Cold Spring Harbor, N.Y.
23. Wong, K. K. (2009) Recent developments in anti-cancer agents targeting the Ras/Raf/MEK/ERK pathway. *Recent Pat Anticancer Drug Discov*, 4, 28-35.
24. Tap, W. D., Gong, K. W., Dering, J., Tseng, Y., Ginther, C., Pauletti, G., Glaspy, J. A., Essner, R., Bollag, G., Hirth, P. et al. (2010) Pharmacodynamic characterization of the efficacy signals due to selective BRAF inhibition with PLX4032 in malignant melanoma. *Neoplasia*, 12, 637-649.
25. Li, J. and Makrigiorgos, G. M. (2009) COLD-PCR: a new platform for highly improved mutation detection in cancer and genetic testing. *Biochem Soc Trans*, 37, 427-432.
26. Tran, N. H., Wu, X. and Frost, J. A. (2005) B-Raf and Raf-1 are regulated by distinct autoregulatory mechanisms. *J Biol Chem*, 280, 16244-16253.
27. Seth, R., Crook, S., Ibrahem, S., Fadhil, W., Jackson, D. and Ilyas, M. (2009) Concomitant mutations and splice variants in KRAS and BRAF demonstrate complex perturbation of the Ras/Raf signalling pathway in advanced colorectal cancer. *Gut*, 58, 1234-1241.
28. Fensterle, J., Becker, J. C., Potapenko, T., Heimbach, V., Vetter, C. S., Brocker, E. B. and Rapp, U. R. (2004) B-Raf specific antibody responses in melanoma patients. *BMC Cancer*, 4, 62.
29. Auger, I., Balandraud, N., Rak, J., Lambert, N., Martin, M. and Roudier, J. (2009) New autoantigens in rheumatoid arthritis (RA): screening 8268 protein arrays with sera from patients with RA. *Ann Rheum Dis*, 68, 591-594.
30. Yu, H., McDaid, R., Lee, J., Possik, P., Li, L., Kumar, S. M., Elder, D. E., Van Belle, P., Gimotty, P., Guerra, M. et al. (2009) The role of BRAF mutation and p53 inactivation during transformation of a subpopulation of primary human melanocytes. *Am J Pathol*, 1.74, 2367-2377.
31. Inazuka, M., Tahira, T., Horiuchi, T., Harashima, S., Sawabe, T., Kondo, M., Miyahara, H. and Hayashi, K. (2000) Analysis of p53 tumour suppressor gene somatic mutations in rheumatoid arthritis synovium. *Rheumatology (Oxford)*, 39, 262-266.
32. Yamanishi, Y., Boyle, D. L., Green, D. R., Keystone, E. C., Connor, A., Zollman, S. and Firestein, G. S. (2005) p53 tumor suppressor gene mutations in fibroblast-like synoviocytes from erosion synovium and non-erosion synovium in rheumatoid arthritis. *Arthritis Res Ther*, 7, R12-18.
33. Karasarides, M., Chiloeches, A., Hayward, R., Niculescu-Duvaz, D., Scanlon, I., Friedlos, F., Ogilvie, L., Hedley, D., Martin, J., Marshall, C. J. et al. (2004) B-RAF is a therapeutic target in melanoma. *Oncogene*, 23, 6292-6298.

What is claimed is:

1. A method for determining whether a subject is suffering from a rheumatoid arthritis associated with a BRAF oncogene, comprising:
   a. contacting a sample from a synovial tissue from the subject with an agent directed to the BRAF oncogene; and
   b. culturing the sample of (a) in the presence of the agent and determining whether BRAF oncogene expression by synovial cells is decreased and/or whether the synovial cells in the sample return to a less transformed phenotype, exhibit decreased synovial cell proliferation and/or exhibit increased contact inhibition by synovial cells, any of which is indicative that the subject is suffering from a rheumatoid arthritis associated with the BRAF oncogene.

2. The method of claim 1, wherein the agent that binds the BRAF oncogene is a nucleic acid molecule.

3. The method of claim 2, wherein the nucleic acid molecule is a RNA molecule.

4. The method of claim 3, wherein the RNA molecule is a siRNA molecule or an anti-sense RNA molecule.

5. The method of claim 1, wherein in the BRAF oncogene of SEQ ID NO:1, a mutation is made so that the codon encoding valine at amino acid position 600 of SEQ ID NO:2 is changed so that the changed codon encodes an amino acid other than valine.

6. The method of claim 1, wherein the BRAF oncogene is an alternatively spliced BRAF transcript as shown in SEQ ID NO:1 which is missing the nucleic acid sequence beginning at nucleotide position 241 to nucleotide position 1140 so that it encodes a mutant BRAF protein as shown in SEQ ID NO:2 but which is missing an amino acid sequence beginning at amino acid position 81 through amino acid position 380 of SEQ ID NO:2.

7. The method of claim 1, wherein the BRAF oncogene is an alternatively spliced BRAF transcript as shown in SEQ ID NO:1 which is missing the nucleic acid sequence beginning at nucleotide position 505 to nucleotide position 1992 so that it encodes a mutant BRAF protein shown in SEQ ID NO:2 but which is missing an amino acid sequence beginning at amino acid position 169 through amino acid position 664.

8. The method of claim 1, wherein the BRAF oncogene is an alternatively spliced BRAF transcript as shown in SEQ ID NO:1 which is missing the nucleic acid sequence beginning at nucleotide position 139 to nucleotide position 1992 so that it encodes a mutant BRAF protein shown in SEQ ID NO:2 but which is missing an amino acid sequence beginning at amino acid position 47 through amino acid position 664.

9. The method of claim 1, wherein the BRAF oncogene is an alternatively spliced BRAF transcript as shown in SEQ ID NO:1 which is missing the nucleic acid sequence beginning at nucleotide position 139 to nucleotide position 1860 so that it encodes a mutant BRAF protein shown in SEQ ID NO:2 but which is missing an amino acid sequence beginning at amino acid position 47 through amino acid position 620.

10. The method of claim 1, wherein the BRAF oncogene is an alternatively spliced BRAF transcript as shown in SEQ ID NOM which is missing the nucleic acid sequence beginning at nucleotide position 505 to nucleotide position 1695 so that it encodes a mutant BRAF protein shown in SEQ ID NO:2 but which is missing amino acid sequence beginning at amino acid position 169 and ending at amino acid position 565.

11. A method for determining whether a subject is suffering from a rheumatoid arthritis associated with the BRAF oncogene comprising:
    a. Contacting a sample from a synovial tissue of the subject with an agent directed to the BRAF oncogene or its transcript(s);
    b. Detecting association of the agent with the BRAF oncogene or its transcript(s) from synovial cells of the synovial tissue, such association being indicative that the subject is suffering from a rheumatoid arthritis associated with the BRAF oncogene, wherein the BRAF oncogene has a mutation so that the codon encoding valine at amino acid position 600 of SEQ ID NO:2 is changed to codon which encodes arginine or an amino acid other than valine.

12. The method of claim 11, wherein the agent that binds the BRAF oncogene is a nucleic acid molecule.

13. The method of claim 12, wherein the nucleic acid molecule is a RNA molecule.

14. The method of claim 13, wherein the RNA molecule is a siRNA molecule or an anti-sense RNA molecule.

15. A method for inhibiting synovial cell growth in a subject suffering from rheumatoid arthritis associated with the BRAF oncogene comprising contacting the synovial cell with an agent that binds the BRAF oncogene and thereby inhibiting synovial cell growth in a subject suffering from the rheumatoid arthritis associated with the BRAF oncogene.

16. The method of claim 15, wherein the molecule that targets the BRAF oncogene is a nucleic acid molecule.

17. The method of claim 16, wherein the nucleic acid molecule is a RNA molecule.

* * * * *